(12) United States Patent
Rajagopalan et al.

(10) Patent No.: US 11,826,521 B2
(45) Date of Patent: Nov. 28, 2023

(54) SYSTEMS, DEVICES AND METHODS FOR THE CREATION OF A THERAPEUTIC RESTRICTION IN THE GASTROINTESTINAL TRACT

(71) Applicant: Fractyl Health, Inc., Lexington, MA (US)

(72) Inventors: Harith Rajagopalan, Wellesley Hills, MA (US); Jay Caplan, Belmont, MA (US); R. Maxwell Flaherty, Topsfield, MA (US); J. Christopher Flaherty, Auburndale, FL (US)

(73) Assignee: Fractyl Health, Inc., Lexington, MA (US)

( * ) Notice: Subject to any disclaimer, the term of this patent is extended or adjusted under 35 U.S.C. 154(b) by 338 days.

(21) Appl. No.: 17/095,108

(22) Filed: Nov. 11, 2020

(65) Prior Publication Data

US 2021/0299404 A1 Sep. 30, 2021

Related U.S. Application Data

(63) Continuation of application No. 16/267,771, filed on Feb. 5, 2019, now Pat. No. 10,864,352, which is a
(Continued)

(51) Int. Cl.
*A61M 25/00* (2006.01)
*A61F 5/00* (2006.01)
(Continued)

(52) U.S. Cl.
CPC ....... *A61M 25/0084* (2013.01); *A61F 5/0013* (2013.01); *A61F 5/0076* (2013.01);
(Continued)

(58) Field of Classification Search
CPC .... A61F 5/0003; A61F 5/0013; A61F 5/0069; A61M 25/0084
See application file for complete search history.

(56) References Cited

U.S. PATENT DOCUMENTS 5,084,044 A 1/1992 Quint
5,190,540 A 3/1993 Lee
(Continued)

FOREIGN PATENT DOCUMENTS

CA 2666661 C 1/2015
CN 1771888 A 5/2006
(Continued)

OTHER PUBLICATIONS

Adams, et al. Theoretical design and evaluation of endoluminal ultrasound applicators for thermal therapy of pancreatic cancer under image guidance. AIP Conference Proceedings 1821, 110002 (2017); doi: http://dx.doi.org/10.1063/1.4977640.
(Continued)

*Primary Examiner* — Jason-Dennis N Stewart
(74) *Attorney, Agent, or Firm* — Wilson Sonsini Goodrich & Rosati

(57) ABSTRACT

A system for treating a patient comprises a delivery device and injectate. The delivery device comprises an elongate shaft with a distal portion and at least one delivery element positioned on the elongate shaft distal portion. The delivery device is constructed and arranged to deliver the injectate through the at least one delivery element and into tissue to create a therapeutic restriction in the gastrointestinal tract. Methods of creating a therapeutic restriction are also provided.

12 Claims, 11 Drawing Sheets

Related U.S. Application Data continuation of application No. 15/156,585, filed on May 17, 2016, now Pat. No. 10,232,143, which is a continuation of application No. PCT/US2014/066829, filed on Nov. 21, 2014.

(60) Provisional application No. 61/907,808, filed on Nov. 22, 2013.

(51) Int. Cl.

| | | |
|---|---|---|
| *A61M 31/00* | (2006.01) | |
| *A61K 45/06* | (2006.01) | |
| *A61K 31/728* | (2006.01) | |
| *A61K 33/42* | (2006.01) | |
| *A61K 35/33* | (2015.01) | |
| *A61K 35/35* | (2015.01) | |
| *A61L 31/04* | (2006.01) | |
| *A61L 31/06* | (2006.01) | |
| *A61L 31/14* | (2006.01) | |
| *A61L 31/16* | (2006.01) | |
| *A61N 1/30* | (2006.01) | |

(52) U.S. Cl.
CPC .......... *A61K 31/728* (2013.01); *A61K 33/42* (2013.01); *A61K 35/33* (2013.01); *A61K 35/35* (2013.01); *A61K 45/06* (2013.01); *A61L 31/043* (2013.01); *A61L 31/048* (2013.01); *A61L 31/06* (2013.01); *A61L 31/145* (2013.01); *A61L 31/16* (2013.01); *A61M 25/00* (2013.01); *A61M 25/0082* (2013.01); *A61M 31/00* (2013.01); *A61F 2005/0016* (2013.01); *A61M 2025/0089* (2013.01); *A61M 2025/0096* (2013.01); *A61N 1/306* (2013.01)

(56) References Cited

U.S. PATENT DOCUMENTS

| | | |
|---|---|---|
| 5,423,754 A | 6/1995 | Cornelius et al. |
| 5,471,982 A | 12/1995 | Edwards et al. |
| 5,496,311 A | 3/1996 | Abele et al. |
| 5,515,100 A | 5/1996 | Nogo |
| 5,542,928 A | 8/1996 | Evans et al. |
| 5,549,559 A | 8/1996 | Eshel |
| 5,575,772 A | 11/1996 | Lennox |
| 5,704,934 A | 1/1998 | Neuwirth et al. |
| 5,730,719 A | 3/1998 | Edwards |
| 5,800,484 A | 9/1998 | Gough et al. |
| 5,827,269 A | 10/1998 | Saadat |
| 5,859,037 A | 1/1999 | Whitcomb et al. |
| 5,869,037 A | 2/1999 | Crystal et al. |
| 5,871,525 A | 2/1999 | Edwards et al. |
| 5,879,347 A | 3/1999 | Saadat et al. |
| 5,957,962 A | 9/1999 | Wallsten et al. |
| 5,964,753 A | 10/1999 | Edwards |
| 6,009,877 A | 1/2000 | Edwards |
| 6,053,937 A | 4/2000 | Edwards et al. |
| 6,056,744 A | 5/2000 | Edwards et al. |
| 6,066,132 A | 5/2000 | Chen et al. |
| 6,077,257 A | 6/2000 | Edwards et al. |
| 6,112,123 A | 8/2000 | Kelleher et al. |
| 6,293,909 B1 | 9/2001 | Chu et al. |
| 6,325,777 B1 | 12/2001 | Zadno-Azizi et al. |
| 6,325,798 B1 | 12/2001 | Edwards et al. |
| 6,338,726 B1 | 1/2002 | Edwards et al. |
| 6,358,245 B1 | 3/2002 | Edwards et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,425,887 B1 | 7/2002 | Mcguckin et al. |
| 6,443,947 B1 | 9/2002 | Marko et al. |
| 6,544,226 B1 | 4/2003 | Gaiser et al. |
| 6,673,070 B2 | 1/2004 | Edwards et al. |
| 6,712,814 B2 | 3/2004 | Edwards et al. |
| 6,802,841 B2 | 10/2004 | Utley et al. |
| 6,905,496 B1 | 6/2005 | Ellman et al. |
| 6,962,587 B2 | 11/2005 | Johnson et al. |
| 6,974,456 B2 | 12/2005 | Edwards et al. |
| 7,077,841 B2 | 7/2006 | Gaiser et al. |
| 7,111,627 B2 | 9/2006 | Stack et al. |
| 7,122,031 B2 | 10/2006 | Edwards et al. |
| 7,125,407 B2 | 10/2006 | Edwards et al. |
| 7,156,860 B2 | 1/2007 | Wallsten |
| 7,165,551 B2 | 1/2007 | Edwards et al. |
| 7,241,295 B2 | 7/2007 | Maguire |
| 7,326,207 B2 | 2/2008 | Edwards |
| 7,371,215 B2 | 5/2008 | Colliou et al. |
| 7,387,626 B2 | 6/2008 | Edwards et al. |
| 7,422,587 B2 | 9/2008 | Bek et al. |
| 7,507,234 B2 | 3/2009 | Utley et al. |
| 7,507,238 B2 | 3/2009 | Utley et al. |
| 7,530,979 B2 | 5/2009 | Ganz et al. |
| 7,556,628 B2 | 7/2009 | Utley et al. |
| 7,585,296 B2 | 9/2009 | Edward et al. |
| 7,632,268 B2 | 12/2009 | Utley et al. |
| 7,632,291 B2 | 12/2009 | Stephens et al. |
| 7,648,500 B2 | 1/2010 | Edwards et al. |
| 7,758,623 B2 | 7/2010 | Dzeng et al. |
| 7,762,977 B2 | 7/2010 | Porter et al. |
| 7,947,038 B2 | 5/2011 | Edwards |
| 7,959,627 B2 | 6/2011 | Utley et al. |
| 7,993,336 B2 | 8/2011 | Jackson et al. |
| 7,997,278 B2 | 8/2011 | Utley et al. |
| 8,012,149 B2 | 9/2011 | Jackson et al. |
| 8,066,689 B2 | 11/2011 | Mitelberg et al. |
| 8,152,803 B2 | 4/2012 | Edwards et al. |
| 8,177,853 B2 | 5/2012 | Stack et al. |
| 8,192,426 B2 | 6/2012 | Stern et al. |
| 8,251,992 B2 | 8/2012 | Utley et al. |
| 8,273,012 B2 | 9/2012 | Wallace et al. |
| 8,323,229 B2 | 12/2012 | Shin et al. |
| 8,364,237 B2 | 1/2013 | Stone et al. |
| 8,377,055 B2 | 2/2013 | Jackson et al. |
| 8,486,005 B2 | 7/2013 | Yodfat et al. |
| 8,641,711 B2 | 2/2014 | Kelly et al. |
| 8,740,894 B2 | 6/2014 | Edwards |
| 8,790,705 B2 | 7/2014 | Geigle et al. |
| 9,364,283 B2 | 6/2016 | Utley et al. |
| 9,555,020 B2 | 1/2017 | Pasricha et al. |
| 9,615,880 B2 | 4/2017 | Gittard et al. |
| 9,757,535 B2 | 9/2017 | Rajagopalan et al. |
| 9,844,641 B2 | 12/2017 | Rajagopalan et al. |
| 10,232,143 B2 | 3/2019 | Rajagopalan et al. |
| 10,299,857 B2 | 5/2019 | Rajagopalan et al. |
| 10,349,998 B2 | 7/2019 | Levin et al. |
| 10,610,663 B2 | 4/2020 | Rajagopalan et al. |
| 10,765,474 B2 | 9/2020 | Kadamus et al. |
| 10,864,352 B2 | 12/2020 | Rajagopalan et al. |
| 10,869,718 B2 | 12/2020 | Rajagopalan et al. |
| 2002/0013581 A1 | 1/2002 | Edwards et al. |
| 2002/0077594 A1 | 6/2002 | Chien et al. |
| 2002/0115992 A1 | 8/2002 | Utley et al. |
| 2002/0192162 A1 | 12/2002 | Green |
| 2003/0040804 A1 | 2/2003 | Stack et al. |
| 2003/0093072 A1 | 5/2003 | Friedman |
| 2003/0153905 A1 | 8/2003 | Edwards et al. |
| 2003/0233065 A1 | 12/2003 | Steward et al. |
| 2004/0082859 A1 | 4/2004 | Schaer |
| 2004/0087936 A1 | 5/2004 | Stern et al. |
| 2004/0133256 A1 | 7/2004 | Callister |
| 2004/0148034 A1 | 7/2004 | Kagan et al. |
| 2004/0204768 A1 | 10/2004 | Geitz |
| 2004/0215180 A1 | 10/2004 | Starkebaum et al. |
| 2004/0215296 A1 | 10/2004 | Ganz et al. |
| 2004/0220559 A1 | 11/2004 | Kramer et al. |
| 2005/0096638 A1 | 5/2005 | Starkebaum et al. |
| 2005/0154386 A1 | 7/2005 | West et al. |
| 2005/0165437 A1 | 7/2005 | Takimoto |
| 2005/0171524 A1 | 8/2005 | Stern et al. |
| 2005/0192652 A1 | 9/2005 | Cioanta et al. |
| 2005/0203489 A1 | 9/2005 | Saadat et al. |
| 2005/0222558 A1 | 10/2005 | Baxter et al. |

(56) References Cited

U.S. PATENT DOCUMENTS

| | | |
|---|---|---|
| 2005/0245943 A1 | 11/2005 | Zvuloni et al. |
| 2005/0246037 A1 | 11/2005 | Starkebaum |
| 2005/0251116 A1 | 11/2005 | Steinke et al. |
| 2005/0273090 A1 | 12/2005 | Nieman et al. |
| 2006/0070631 A1 | 4/2006 | Scopton et al. |
| 2006/0118127 A1 | 6/2006 | Chinn |
| 2006/0135963 A1 | 6/2006 | Kick et al. |
| 2006/0155261 A1 | 7/2006 | Bek et al. |
| 2006/0205992 A1 | 9/2006 | Lubock et al. |
| 2006/0247683 A1 | 11/2006 | Danek et al. |
| 2006/0257444 A1 | 11/2006 | Tropsha et al. |
| 2006/0259030 A1 | 11/2006 | Utley et al. |
| 2006/0293742 A1 | 12/2006 | Dann et al. |
| 2007/0016262 A1 | 1/2007 | Gross et al. |
| 2007/0032788 A1 | 2/2007 | Edwards et al. |
| 2007/0100355 A1 | 5/2007 | Bonde et al. |
| 2008/0045785 A1 | 2/2008 | Oyatsu |
| 2008/0107744 A1 | 5/2008 | Chu |
| 2008/0119788 A1 | 5/2008 | Winter |
| 2008/0125760 A1 | 5/2008 | Gilboa |
| 2008/0125803 A1 | 5/2008 | Sadamasa et al. |
| 2008/0147056 A1 | 6/2008 | Van et al. |
| 2008/0207994 A1 | 8/2008 | Gonon |
| 2008/0243112 A1 | 10/2008 | De |
| 2008/0275445 A1 | 11/2008 | Kelly et al. |
| 2008/0319504 A1 | 12/2008 | Loushin et al. |
| 2009/0012469 A1 | 1/2009 | Nita |
| 2009/0012512 A1 | 1/2009 | Utley et al. |
| 2009/0012518 A1 | 1/2009 | Utley et al. |
| 2009/0018533 A1 | 1/2009 | Perkins et al. |
| 2009/0018603 A1 | 1/2009 | Mitelberg et al. |
| 2009/0018604 A1 | 1/2009 | Mitelberg et al. |
| 2009/0048593 A1 | 2/2009 | Ganz et al. |
| 2009/0069805 A1 | 3/2009 | Fischer et al. |
| 2009/0270851 A1 | 10/2009 | Babkin et al. |
| 2010/0022891 A1 | 1/2010 | Zuluaga et al. |
| 2010/0030190 A1 | 2/2010 | Singh |
| 2010/0114087 A1 | 5/2010 | Edwards et al. |
| 2010/0114325 A1 | 5/2010 | Yang et al. |
| 2010/0168561 A1 | 7/2010 | Anderson |
| 2010/0168624 A1 | 7/2010 | Sliwa |
| 2010/0204673 A1 | 8/2010 | Miller |
| 2010/0204688 A1 | 8/2010 | Hoey et al. |
| 2010/0217151 A1 | 8/2010 | Gostout et al. |
| 2010/0234840 A1 | 9/2010 | Jackson et al. |
| 2010/0256775 A1 | 10/2010 | Belhe et al. |
| 2010/0260703 A1 | 10/2010 | Yankelson et al. |
| 2011/0046537 A1 | 2/2011 | Errico et al. |
| 2011/0091564 A1 | 4/2011 | Chu |
| 2011/0106273 A1 | 5/2011 | Belhe et al. |
| 2011/0160648 A1 | 6/2011 | Hoey |
| 2011/0172659 A1 | 7/2011 | Brannan |
| 2011/0184401 A1 | 7/2011 | Iwata et al. |
| 2011/0319809 A1 | 12/2011 | Smith |
| 2012/0004654 A1 | 1/2012 | Jackson et al. |
| 2012/0016364 A1 | 1/2012 | Mayse et al. |
| 2012/0059364 A1 | 3/2012 | Baust et al. |
| 2012/0197245 A1 | 8/2012 | Burnett et al. |
| 2012/0271277 A1 | 10/2012 | Fischell et al. |
| 2012/0271301 A1 | 10/2012 | Fischell et al. |
| 2012/0289952 A1 | 11/2012 | Utley et al. |
| 2013/0071466 A1 | 3/2013 | Chancellor et al. |
| 2013/0178910 A1 | 7/2013 | Azamian et al. |
| 2013/0345670 A1 | 12/2013 | Rajagopalan et al. |
| 2014/0031773 A1 | 1/2014 | Mikkaichi |
| 2014/0074077 A1 | 3/2014 | Lane |
| 2014/0088529 A1 | 3/2014 | Bengtson |
| 2014/0121646 A1 | 5/2014 | Lodin et al. |
| 2014/0135661 A1 | 5/2014 | Garrison et al. |
| 2014/0163664 A1 | 6/2014 | Goldsmith |
| 2014/0187619 A1 | 7/2014 | Pasricha et al. |
| 2014/0255458 A1 | 9/2014 | Li et al. |
| 2014/0324037 A1 | 10/2014 | Hoey et al. |
| 2014/0371736 A1 | 12/2014 | Levin et al. |
| 2015/0045825 A1 | 2/2015 | Caplan et al. |
| 2015/0141987 A1 | 5/2015 | Caplan et al. |
| 2015/0148738 A1 | 5/2015 | Caplan et al. |
| 2015/0359594 A1 | 12/2015 | Ben-Oren et al. |
| 2016/0008050 A1 | 1/2016 | Rajagopalan et al. |
| 2016/0081745 A1 | 3/2016 | Rajagopalan et al. |
| 2016/0310200 A1 | 10/2016 | Wang |
| 2016/0354144 A1 | 12/2016 | Caplan et al. |
| 2017/0007324 A1 | 1/2017 | Kadamus et al. |
| 2017/0014596 A1 | 1/2017 | Rajagopalan et al. |
| 2017/0191035 A1 | 7/2017 | Sia et al. |
| 2018/0193078 A1 | 7/2018 | Rajagopalan et al. |
| 2018/0193590 A1 | 7/2018 | Rajagopalan et al. |
| 2018/0221622 A1 | 8/2018 | Rajagopalan et al. |
| 2020/0060758 A1 | 2/2020 | Rajagopalan et al. |
| 2020/0060942 A1 | 2/2020 | Rajagopalan et al. |
| 2020/0138505 A1 | 5/2020 | Levin et al. |
| 2020/0155217 A1 | 5/2020 | Morneau et al. |
| 2020/0261144 A1 | 8/2020 | Caplan et al. |
| 2020/0305972 A1 | 10/2020 | Kadamus et al. |
| 2020/0405388 A1 | 12/2020 | Rajagopalan et al. |
| 2021/0008336 A1 | 1/2021 | Rajagopalan et al. |

FOREIGN PATENT DOCUMENTS

| | | |
|---|---|---|
| CN | 101212932 A | 7/2008 |
| CN | 102470038 A | 5/2012 |
| EP | 1698296 A1 | 9/2006 |
| EP | 1886634 A1 | 2/2008 |
| EP | 3071286 A1 | 9/2016 |
| JP | 2002503512 A | 2/2002 |
| JP | 2003520068 A | 7/2003 |
| JP | 2004500184 A | 1/2004 |
| JP | 2004180934 A | 7/2004 |
| JP | 2006509536 A | 3/2006 |
| JP | 2006136726 A | 6/2006 |
| JP | 2007502690 A | 2/2007 |
| JP | 2008515464 A | 5/2008 |
| JP | 2010142661 A | 7/2010 |
| JP | 2010533036 A | 10/2010 |
| JP | 2011517599 A | 6/2011 |
| JP | 2012071148 A | 4/2012 |
| JP | 2013543423 A | 12/2013 |
| JP | 2014503256 A | 2/2014 |
| KR | 20080013945 A | 2/2008 |
| WO | WO-9418896 A1 | 9/1994 |
| WO | WO-9912489 A2 | 3/1999 |
| WO | WO-0207628 A2 | 1/2002 |
| WO | WO-02058577 A1 | 8/2002 |
| WO | WO-02096327 A2 | 12/2002 |
| WO | WO-02102453 A2 | 12/2002 |
| WO | WO-03033045 A2 | 4/2003 |
| WO | WO-03092609 A2 | 11/2003 |
| WO | WO-2004064600 A2 | 8/2004 |
| WO | WO-2006020370 A2 | 2/2006 |
| WO | WO-2007044244 A2 | 4/2007 |
| WO | WO-2007067919 A2 | 6/2007 |
| WO | WO-2008002654 A2 | 1/2008 |
| WO | WO-2010042461 A1 | 4/2010 |
| WO | WO-2010125570 A1 | 11/2010 |
| WO | WO-2011060301 A1 | 5/2011 |
| WO | WO-2012009486 A2 | 1/2012 |
| WO | WO-2012099974 A2 | 7/2012 |
| WO | WO-2013130655 A1 | 9/2013 |
| WO | WO-2013134541 A2 | 9/2013 |
| WO | WO-2013159066 A1 | 10/2013 |
| WO | WO-2014022436 A1 | 2/2014 |
| WO | WO-2014026055 A1 | 2/2014 |
| WO | WO-2014055997 A1 | 4/2014 |
| WO | WO-2014070136 A1 | 5/2014 |
| WO | WO-2014197632 A2 | 12/2014 |
| WO | WO-2015038973 A1 | 3/2015 |
| WO | WO-2015077571 A1 | 5/2015 |
| WO | WO-2015148541 A1 | 10/2015 |
| WO | WO-2016011269 A1 | 1/2016 |
| WO | WO-2017004432 A1 | 1/2017 |
| WO | WO-2018089773 A1 | 5/2018 |

(56) References Cited

FOREIGN PATENT DOCUMENTS

| | | |
|---|---|---|
| WO | WO-2019018362 A1 | 1/2019 |
| WO | WO-2019136240 A1 | 7/2019 |

OTHER PUBLICATIONS

Chathadi, et al. The role of endoscopy in ampullary and duodenal adenomas. Gastrointest Endosc. Nov. 2015;82(5):773-81. doi: 10.1016/j.gie.2015.06.027. Epub Aug. 7, 2015.
Cherrington, et al. Hydrothermal Duodenal Mucosal Resurfacing: Role in the Treatment of Metabolic Disease. Gastrointest Endosc Clin N Am. Apr. 2017;27(2):299-311. doi: 10.1016/j.giec.2016.12.002.
Co-pending U.S. Appl. No. 16/905,274, inventors Rajagopalan; Harith et al., filed Jun. 18, 2020.
Co-pending U.S. Appl. No. 17/096,855, inventors Rajagopalan; Harith et al., filed Nov. 12, 2020.
Co-pending U.S. Appl. No. 17/110,720, inventors J.; Kadamus Christopher J. et al., filed Dec. 3, 2020.
EP12736438.8 The Extended European Search Report dated Nov. 22, 2016.
EP14844285.8 The Extended European Search Report dated Apr. 25, 2017.
EP20150391.9 The Extended European Search Report dated Aug. 20, 2020.
EP20159816.6 The Extended European Search Report dated Aug. 17, 2020.
European search report and search opinion dated Mar. 8, 2016 for EP Application No. 13825257.2.
European search report and search opinion dated Mar. 17, 2016 for EP Application No. 13827149.9.
European search report and search opinion dated Aug. 4, 2015 for EP Application No. 13755156.0.
European Search Report and Search Opinion dated Aug. 7, 2017 for European Patent Application No. EP14864511.2.
European Search Report and Search Opinion dated Aug. 7, 2017 for European Patent Application No. EP15768945.6.
European search report and search opinion dated Nov. 25, 2015 for EP Application No. 13777572.2.
European search report with written opinion dated Feb. 1, 2018 for EP Application No. 15822378.
European search report with written opinion dated Dec. 2, 2016 for EP Application No. 14807116.
Final Office action dated Mar. 22, 2019 for U.S. Appl. No. 14/917,243.
Final Office action dated Apr. 5, 2019 for U.S. Appl. No. 14/609,334.
Final Office action dated Jun. 17, 2019 for U.S. Appl. No. 14/609,332.
Final Office action dated Jul. 10, 2019 for U.S. Appl. No. 15/274,948.
Galvao Neto, et al. Endoscopic Duodenal Mucosal Resurfacing Improves Glycemic and Hepatic Parameters in Patients With Type 2 Diabetes: Data From a First-in-Human Study. Gastroenterology. 829. Apr. 2016, vol. 150, Issue 4, Supplement 1, p. S174. 1 page. DOI: http://dx.doi.org/10.1016/S0016-5085(16)30672-2.
Grikscheit, et al. Tissue-engineered small intestine improves recovery after massive small bowel resection. Ann Surg., 2004, 240:748-754.
International search report and written opinion dated Feb. 20, 2015 for PCT Application No. US2014/711601.
International search report and written opinion dated Jun. 21, 2013 for PCT Application No. US2013/028082.
International search report and written opinion dated Jun. 26, 2015 for PCT Application No. US2015/022293.
International search report and written opinion dated Jul. 13, 2012 for PCT Application No. US2012/021739.
International search report and written opinion dated Aug. 8, 2013 for PCT Application No. US2013/037485.
International Search Report and Written Opinion dated Sep. 22, 2016 for International PCT Patent Application No. PCT/US2016/040512.
International search report and written opinion dated Oct. 23, 2015 for PCT/US2015/040775.
International search report and written opinion dated Nov. 8, 2013 for PCT Application No. US2013/052786.
International search report and written opinion dated Nov. 11, 2013 for PCT Application No. US2013/054219.
International search report and written opinion dated Dec. 24, 2014 for PCT Application No. US2014/055514.
International search report and written opinion dated Dec. 30, 2013 for PCT Application No. US2013/063753.
International search report dated Dec. 3, 2014 for PCT Application No. US2014/040957.
International search report with written opinion dated Jan. 9, 2018 for PCT/US2017/061074.
Miyawaki, et al. Inhibition of gastric inhibitory polypeptide signaling prevents obesity. Nat Med. Jul. 2002;8(7):738-42. Epub Jun. 17, 2002.
Notice of Allowance dated Jul. 7, 2017 for U.S. Appl. No. 15/274,764.
Notice of Allowance dated Sep. 14, 2017 for U.S. Appl. No. 15/274,809.
Office Action dated Jul. 11, 2018 for U.S. Appl. No. 14/917,243.
Office Action dated Aug. 9, 2018 for U.S. Appl. No. 14/673,565.
Office action dated Jan. 8, 2018 for U.S. Appl. No. 14/609,334.
Office Action dated Jan. 13, 2017 for U.S. Appl. No. 14/609,332.
Office action dated Feb. 29, 2016 for U.S. Appl. No. 14/609,334.
Office action dated Mar. 7, 2019 for U.S. Appl. No. 13/945,138.
Office Action dated Mar. 7, 2017 for U.S. Appl. No. 15/274,764.
Office Action dated Mar. 7, 2017 for U.S. Appl. No. 15/274,809.
Office action dated Mar. 7, 2019 for U.S. Appl. No. 14/673,565.
Office action dated Mar. 12, 2015 for U.S. Appl. No. 13/945,138.
Office action dated Mar. 19, 2018 for U.S. Appl. No. 14/470,503.
Office Action dated Mar. 23, 2017 for U.S. Appl. No. 13/945,138.
Office action dated Mar. 28, 2016 for U.S. Appl. No. 14/673,565.
Office action dated Apr. 4, 2018 for U.S. Appl. No. 15/156,585.
Office action dated May 16, 2019 for U.S. Appl. No. 14/515,324.
Office action dated May 18, 2018 for U.S. Appl. No. 14/956,710.
Office Action dated May 31, 2017 for U.S. Appl. No. 15/274,764.
Office action dated Jun. 6, 2019 for U.S. Appl. No. 15/683,713.
Office Action dated Jun. 21, 2017 for U.S. Appl. No. 14/515,324.
Office Action dated Jun. 21, 2017 for U.S. Appl. No. 14/609,334.
Office Action dated Jun. 30, 2017 for U.S. Appl. No. 14/470,503.
Office action dated Aug. 5, 2015 for U.S. Appl. No. 13/945,138.
Office action dated Sep. 7, 2018 for U.S. Appl. No. 14/609,332.
Office Action dated Sep. 23, 2016 for U.S. Appl. No. 14/515,324.
Office action dated Oct. 4, 2018 for U.S. Appl. No. 14/515,324.
Office Action dated Oct. 7, 2016 for U.S. Appl. No. 13/945,138.
Office Action dated Nov. 2, 2017 for U.S. Appl. No. 15/156,585.
Office action dated Nov. 2, 2018 for U.S. Appl. No. 14/609,334.
Office Action dated Nov. 15, 2016 for U.S. Appl. No. 14/609,334.
Office action dated Nov. 16, 2017 for U.S. Appl. No. 14/609,332.
Office action dated Nov. 30, 2015 for U.S. Appl. No. 13/945,138.
Office action dated Nov. 30, 2017 for U.S. Appl. No. 14/673,565.
Office action dated Dec. 17, 2015 for U.S. Appl. No. 14/515,324.
Office action dated Dec. 18, 2017 for U.S. Appl. No. 14/515,324.
Office action dated Dec. 18, 2018 for U.S. Appl. No. 14/470,503.
Office action dated Dec. 19, 2017 for U.S. Appl. No. 13/945,138.
PCT/US14/66829 International Search Report dated Feb. 20, 2015.
PCT/US2018/042438 International Search Report dated Sep. 14, 2018.
PCT/US2019/012338 International Search Report dated Apr. 15, 2019.
Rajagopalan, et al. Endoscopic Duodenal Mucosal Resurfacing for the Treatment of Type 2 Diabetes: 6-Month Interim Analysis From the First-in-Human Proof-of-Concept Study. Diabetes Care Dec. 2016; 39(12): 2254-2261. https://doi.org/10.2337/dc16-0383.
Rubino, et al. Potential of surgery for curing type 2 diabetes mellitus. Ann Surg. Nov. 2002;236(5):554-9.
Sarriá, et al. Morphometric study of the layers of the canine small intestine at five sampling sites. Vet J. Jun. 2012;192(3):498-502. doi: 10.1016/j.tvjl.2011.06.041. Epub Nov. 3, 2011.
Semkova, et al. Autologous transplantation of genetically modified iris pigment epithelial cells: A promising concept for the treatment

(56) References Cited

OTHER PUBLICATIONS of age-related macular degeneration and other disorders of the eye. Proc Natl Acad Sci U S A. Oct. 1, 2002; 99(20): 13090-13095.
Sen, et al. Autologous transplantation of endothelial progenitor cells genetically modified by adeno-associated viral vector delivering insulin-like growth factor-1 gene after myocardial infarction. Hum Gene Ther. Oct. 2010;21(10):1327-34.
Tolman, et al. Spectrum of liver disease in type 2 diabetes and management of patients with diabetes and liver disease. Diabetes care 30.3 (2007): 734-743.
Tomizawa, et al. Clinical Outcome of Endoscopic Mucosal Resection (EMR) of Sporadic, Non-Ampullary Duodenal Adenoma (SNADA): Predictor Analysis of Safety and Efficacy From a High Volume U.S. Tertiary Referral Center. Gastrointestinal Endoscopy. 377. May 2017, vol. 85, Issue 5, Supplement, p. AB72. DOI: http://dx.doi.org/10.1016/j.gie.2017.03.089.
U.S. Appl. No. 14/917,243 Office Action dated Jun. 5, 2020.
U.S. Appl. No. 14/515,324 Office Action dated Dec. 4, 2020.
U.S. Appl. No. 14/609,334 Notice of Allowance dated Dec. 10, 2020.
U.S. Appl. No. 14/609,334 Office Action dated Oct. 29, 2020.
U.S. Appl. No. 14/673,565 Office Action dated Jun. 12, 2020.
U.S. Appl. No. 15/274,948 Notice of Allowance dated May 14, 2020.
U.S. Appl. No. 15/274,948 Office Action dated Nov. 20, 2018.
U.S. Appl. No. 15/406,572 Notice of Allowance dated Oct. 28, 2020.
U.S. Appl. No. 15/406,572 Office Action dated Apr. 14, 2020.
U.S. Appl. No. 15/406,572 Office Action dated Feb. 7, 2019.
U.S. Appl. No. 15/406,572 Office Action dated Nov. 15, 2019.
U.S. Appl. No. 15/917,480 Notice of Allowance dated Dec. 17, 2020.
U.S. Appl. No. 15/917,480 Office Action dated Nov. 20, 2020.
U.S. Appl. No. 16/267,771 Notice of Allowance dated Aug. 10, 2020.
U.S. Appl. No. 16/711,236 Office Action dated Dec. 10, 2020.
U.S. Appl. No. 16/900,563 Notice of Allowance dated Dec. 17, 2020.
U.S. Appl. No. 16/900,563 Office Action dated Nov. 9, 2020.
U.S. Appl. No. 13/945,138 Office Action dated Dec. 10, 2019.
U.S. Appl. No. 14/470,503 Notice of Allowance dated Feb. 27, 2019.
U.S. Appl. No. 14/515,324 Office Action dated Mar. 31, 2020.
U.S. Appl. No. 14/609,334 Office Action dated Jan. 8, 2020.
U.S. Appl. No. 14/956,710 Notice of Allowance dated Jan. 9, 2019.
U.S. Appl. No. 15/683,713 Notice of Allowance dated Mar. 10, 2020.
U.S. Appl. No. 15/683,713 Notice of Allowance dated Nov. 27, 2019.
U.S. Appl. No. 15/683,713 Office Action dated Oct. 10, 2019.
U.S. Appl. No. 15/917,480 Office Action dated Jan. 10, 2020.
U.S. Appl. No. 16/267,771 Office Action dated Feb. 6, 2020.
Van Baar, et al. Single Catheter for Duodenal Mucosal Resurfacing Demonstrates Similar Safety Profile with Improved Procedure Time when Compared to Original Dual Catheter: Multicenter Study of Subjects with Type 2 Diabetes. Gastroenterology. Apr. 2017vol. 152, Issue 5, Supplement 1, p. S825. DOI: http://dx.doi.org/10.1016/S0016-5085(17)32851-2.
U.S. Appl. No. 13/945,138 Notice of Allowance dated Dec. 22, 2020.
U.S. Appl. No. 14/673,565 Office Action dated Dec. 24, 2020.
U.S. Appl. No. 15/156,585 Notice of Allowance dated Nov. 1, 2018.
U.S. Appl. No. 15/156,585 Supplemental Notice of Allowability dated Jan. 14, 2019.
U.S. Appl. No. 15/156,585 Supplemental Notice of Allowance dated Feb. 1, 2019.
U.S. Appl. No. 16/267,771 Supplemental Notice of Allowability dated Nov. 16, 2020.
U.S. Appl. No. 16/267,771 Supplemental Notice of Allowability dated Nov. 2, 2020.

FIG 3A
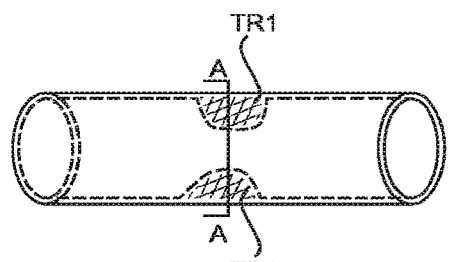 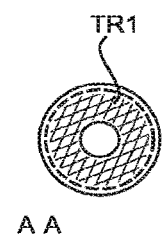
FIG 3B
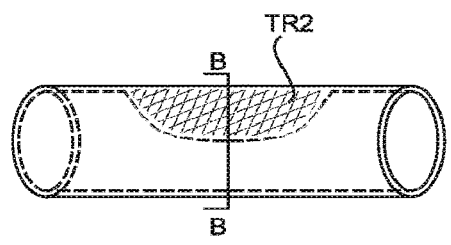 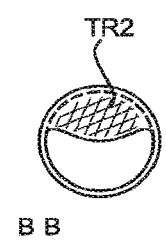
FIG 3C
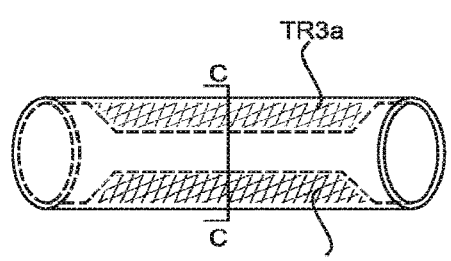 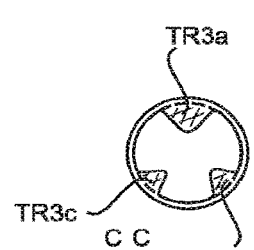
FIG 3D
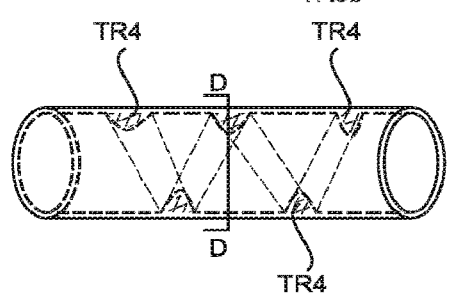 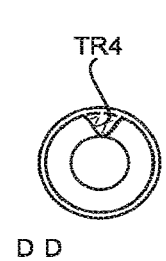

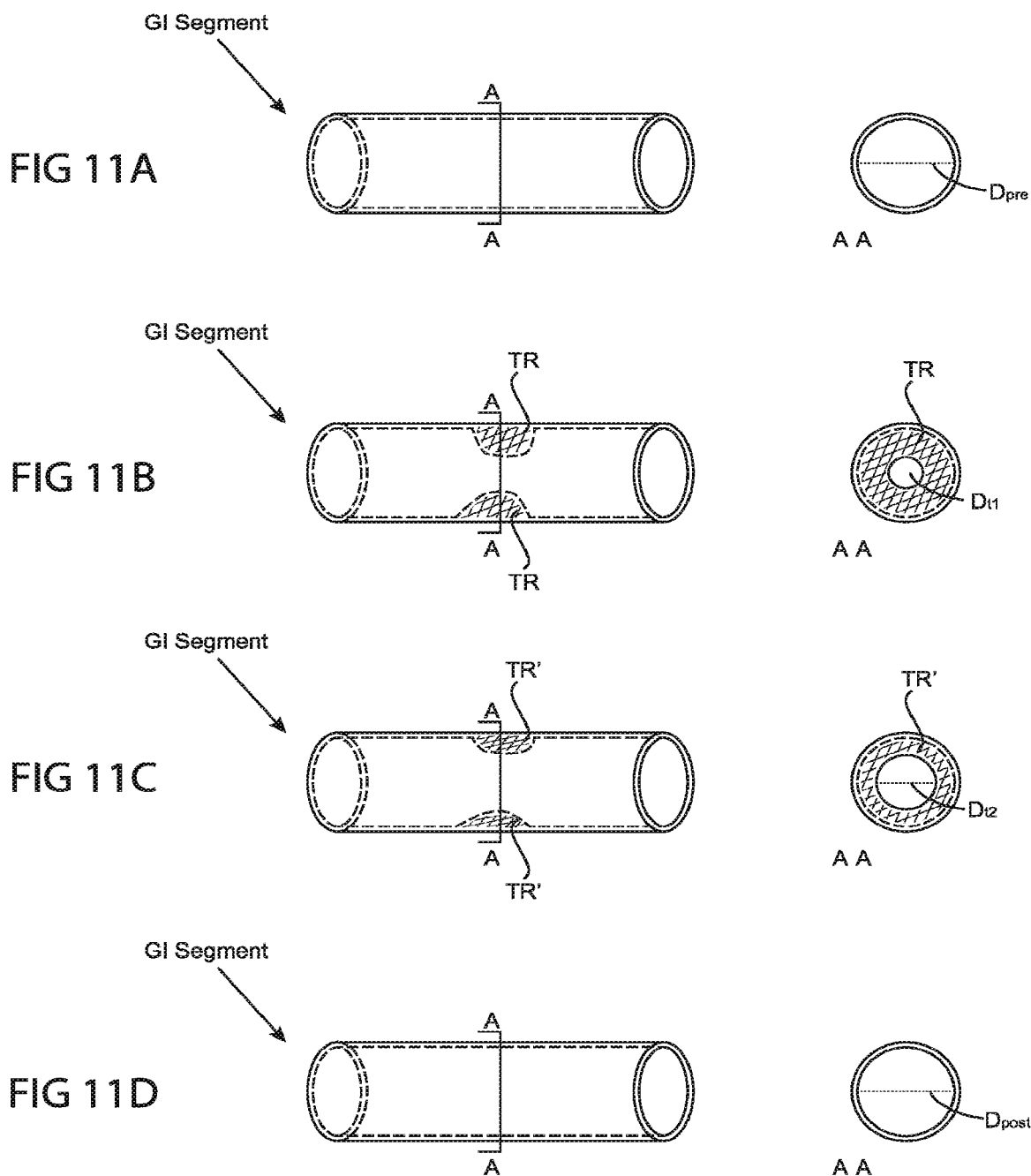

SYSTEMS, DEVICES AND METHODS FOR THE CREATION OF A THERAPEUTIC RESTRICTION IN THE GASTROINTESTINAL TRACT

CROSS-REFERENCE TO RELATED APPLICATIONS

This application is a continuation of U.S. patent application Ser. No. 16/267,771, filed Feb. 5, 2019, which is a continuation of U.S. patent application Ser. No. 15/156,585, filed May 17, 2016, now U.S. Pat. No. 10,232,143, which is a continuation of International Patent Application No. PCT/US2014/066829, filed Nov. 21, 2014, which claims the benefit of U.S. Provisional Patent Application Ser. No. 61/907,808, filed Nov. 22, 2013, the entire content of which is incorporated herein by reference.

This application is related to: U.S. patent application Ser. No. 13/945,138, entitled "Devices and Methods for the Treatment of Tissue", filed Jul. 18, 2013; U.S. patent application Ser. No. 14/470,503, entitled "Heat Ablation Systems, Devices and Methods for the Treatment of Tissue", filed Aug. 27, 2014; U.S. patent application Ser. No. 14/515,324, entitled "Tissue Expansion Devices, Systems and Methods", filed Oct. 15, 2014; International Patent Application Serial Number PCT/US2013/063753, entitled "Methods, Systems and Devices for Performing Multiple Treatments on a Patient", filed Oct. 7, 2013; International Patent Application Serial Number PCT/US2014/040957, entitled "Methods, Systems and Devices for Reducing the Luminal Surface Area of the Gastrointestinal Tract", filed Jun. 4, 2014; and International Patent Application Serial Number PCT/US2014/055514, entitled "Systems, Methods and Devices for Treatment of Target Tissue", filed Sep. 12, 2014; the contents of each of which are incorporated herein by reference in their entirety.

BACKGROUND OF THE INVENTION

Field of the Invention

The present invention relates generally to systems, devices and methods that create a narrowing or other restriction in a patient, such as a restriction in a segment of the gastrointestinal tract of the patient.

Obesity and Type 2 Diabetes are twin epidemics associated with a Western Diet and sedentary lifestyle that are increasing in prevalence at startling rates. Worldwide, there are more than 500 million obese individuals and over 40 million overweight preschool children. Many interventions have been attempted to curb obesity, including steps aimed at preventing obesity and therapies configured to treat obesity in individuals who are already overweight or obese. While a healthy diet and an active lifestyle are key factors in the prevention of obesity, they are inadequate and often ineffective treatments for individuals who are already obese. Certain medical therapies can have a positive impact on weight loss, but they often lead to modest weight loss and require indefinite pharmacologic administration to sustain their treatment benefits.

In addition to lifestyle and medical therapies, an entire field of surgery, called bariatric surgery, has developed to offer surgical solutions for patients seeking dramatic weight loss. Bariatric surgeries fall into three broad categories: restrictive procedures such as laparoscopic adjustable gastric banding (LAGB); intestinal bypass procedures such as the Roux-en-Y gastric bypass (RYGB) and the biliopancreatic diversion (BPD); and gastric reconstructive surgeries such as the sleeve gastrectomy. While mechanistically different and variably effective, these surgeries all share several common features: their clinical science is evolving rapidly, they are very costly, they require inpatient hospitalization, they are permanent, and they are often associated with significant morbidity and mortality.

Against this backdrop, several medical device solutions have been developed to mimic the effects of the surgery while aiming to alleviate some of these challenges mentioned above. While there are many examples of bariatric devices, they fall into four major categories: mucosal barrier devices (such as the duodenal-jejunal barrier), enteric neuromodulation devices, restrictive devices (intraluminal balloons or sutures and extraluminal restrictions), and endoscopic or laparoscopic surgical tools aimed at simplifying the surgery.

All of these approaches require long-term device implants or endoluminal sutures that tend to be poorly tolerated because of the dynamic nature of the GI tract; or they require permanent intestinal surgical alteration that confers significant morbidity and complication risk. Procedures that can mimic the weight loss effects of restrictive surgeries but can be performed expeditiously as an outpatient procedure and/or do not require long-term endoluminal implants, suturing, or intestinal surgery is surely needed. Such a technology should be able to scale to the magnitude of the obesity epidemic without suffering the complication rate and complexity associated with existing approaches.

BRIEF SUMMARY OF THE INVENTION

In one aspect of the present inventive concepts, provided is a method for treating a patient comprising advancing a delivery element to a location proximate a luminal segment of the gastrointestinal tract of the patient; and delivering an injectate through the delivery element and into tissue proximate the luminal segment to create a therapeutic restriction in the luminal segment.

In some embodiments, the therapeutic restriction treats a patient disease or disorder selected from the group consisting of: obesity; type 2 diabetes; type 1 diabetes; hypercholesterolemia; hypertension; metabolic disease; a metabolic syndrome; and combinations thereof. The therapeutic restriction can be created at an anatomical location selected from the group consisting of: lower stomach; pylorus; proximal small intestine; duodenum; proximal jejunum; distal small intestine; distal jejunum; ileum; and combinations thereof.

In some embodiments, the therapeutic restriction is constructed and arranged to restrict the passage of food through a portion of the gastrointestinal tract.

In some embodiments, the therapeutic restriction is constructed and arranged to cause at least one of: early satiety; premature satiety; or satiety.

In some embodiments, the therapeutic restriction is constructed and arranged to alter an absorptive property of the patient.

In some embodiments, the therapeutic restriction is constructed and arranged to alter a secretive property of the patient.

In some embodiments, the therapeutic restriction is constructed and arranged to alter hormonal signaling of the patient.

In some embodiments, the therapeutic restriction is constructed and arranged to treat fecal incontinence. The therapeutic restriction can be created in the colon.

In some embodiments, the therapeutic restriction is created at a location selected from the group consisting of: within mucosal tissue; within submucosal tissue; between mucosal and submucosal tissue; and combinations thereof.

In some embodiments, the therapeutic restriction is created at a location selected from the group consisting of: lower stomach; pylorus; proximal small intestine; duodenum; proximal jejunum; distal small intestine; distal jejunum; ileum; and combinations thereof.

In some embodiments, the therapeutic restriction is created in a location selected from the group consisting of: colon; rectum; anal sphincter and combinations thereof.

In some embodiments, the therapeutic restriction is created by injecting a volume of injectate of at least 1.0 mL. The therapeutic restriction can be created by injecting a volume of injectate of at least 3.0 mL, or at least 4.0 mL.

In some embodiments, the therapeutic restriction is created by injecting a volume of injectate of no more than 20.0 mL. The therapeutic restriction can be created by injecting a volume of injectate of no more than 10.0 mL, or no more than 8.0 mL.

In some embodiments, the therapeutic restriction comprises an axial length between 1 mm and 100 mm. The therapeutic restriction can comprise an axial length between 1 mm and 20 mm.

In some embodiments, the therapeutic restriction comprises an inner diameter (e.g. diameter of its open portion) that is less than or equal to 10 mm. The therapeutic restriction can comprise an inner diameter less than or equal to 5 mm, 4 mm, 3 mm, 2 mm or 1 mm.

In some embodiments, the therapeutic restriction comprises an inner diameter that is between 1% and 50% (e.g. 99% to 50% narrowing, respectively) of the inner diameter of the luminal segment prior to creation of the therapeutic restriction. The therapeutic restriction can comprise an inner diameter that is between 1% and 20% of the inner diameter of the luminal segment prior to creation of the therapeutic restriction. The inner diameter of the therapeutic restriction can increase over time, such as via the therapeutic restriction volume decreasing over time such as via absorption, migration or other reduction of the delivered injectate. The inner diameter of the therapeutic restriction can increase to an inner diameter that is between 11% and 20% of the inner diameter of the luminal segment prior to creation of the therapeutic restriction. The therapeutic restriction can comprise an inner diameter that is between 1% and 10% of the inner diameter of the luminal segment prior to creation of the therapeutic restriction. The therapeutic restriction can comprise an inner diameter that is between 1% and 5% of the inner diameter of the luminal segment prior to creation of the therapeutic restriction.

In some embodiments, at least a portion of the therapeutic restriction comprises a relatively circumferential geometry.

In some embodiments, at least a portion of the therapeutic restriction comprises a partial circumferential geometry.

In some embodiments, at least a portion of the therapeutic restriction comprises a relatively linear geometry.

In some embodiments, at least a portion of the therapeutic restriction comprises a relatively helical geometry.

In some embodiments, the therapeutic restriction comprises a therapeutic restriction dimensional parameter that is based on a patient parameter. The therapeutic restriction dimensional parameter can be selected from the group consisting of: volume; axial length; arc length; surface area; and combinations thereof. The patient parameter can be selected from the group consisting of: body weight; body mass index; excess weight based on established norms; age; HbA1c level; cholesterol level; and combinations thereof.

In some embodiments, the delivery element comprises a first delivery element advanced toward a first luminal segment of the gastrointestinal tract and the injectate comprises a first injectate delivered through the first delivery element and into tissue proximate the first luminal segment to create a first therapeutic restriction in the first luminal segment. The method can further comprise advancing a second delivery element to a similar location and/or to a location proximate a second luminal segment of the gastrointestinal tract of the patient and the method can further comprise delivering a second injectate through the second delivery element and into tissue proximate the second luminal segment to increase the volume of the first therapeutic restriction and/or to create a second therapeutic restriction in the second luminal segment. The second therapeutic restriction can be created based on a patient parameter selected from the group consisting of: body weight; body mass index; excess weight based on established norms; age; HbA1c level; cholesterol level; and combinations thereof. The second therapeutic restriction and the first therapeutic restriction can be created on the same day. The second therapeutic restriction can be created at least one week after the creation of the first therapeutic restriction. The second therapeutic restriction can be positioned at least 5 mm from the first therapeutic restriction. The second therapeutic restriction can be positioned at least 10 mm from the first therapeutic restriction. The first therapeutic restriction can comprise a first geometry and the second therapeutic restriction can comprise a second geometry similar to the first geometry. The first therapeutic restriction can comprise a first geometry and the second therapeutic restriction can comprise a second geometry dissimilar to the first geometry. The first injectate can comprise a first material and the second injectate can comprise a second material similar to the first material. The first injectate can comprise a first material and the second injectate can comprise a second material dissimilar to the first material. The first injectate can comprise a first volume and the second injectate can comprise a second volume similar to the first volume. The first injectate can comprise a first volume and the second injectate can comprise a second volume dissimilar to the first volume.

In some embodiments, the injectate comprises an amount of material based on a patient parameter. The patient parameter can be selected from the group consisting of: body weight; body mass index; excess weight based on established norms; age; HbA1c level; cholesterol level; and combinations thereof.

In some embodiments, the injectate comprises an amount of material determined prior to delivery of the injectate into tissue.

In some embodiments, the injectate comprises an amount of material determined during delivery of the injectate into tissue. The amount of material can be determined based on a parameter selected from the group consisting of: pressure within the therapeutic restriction; pressure within tissue proximate the therapeutic restriction; volume of the therapeutic restriction; diameter of the therapeutic restriction; and combinations thereof.

In some embodiments, the therapeutic restriction comprises a volume that decreases over time. The injectate can comprise a first material and a second material, and the second material can be constructed and arranged to remain in the therapeutic restriction for a longer time period than the first material, and the second material can be delivered at least one day after the first material is delivered.

In some embodiments, at least 50% of the injectate remains in the therapeutic restriction (e.g. the remainder has been absorbed, evacuated from the patient and/or migrated within the patient to another body location outside of the therapeutic restriction) at least one month after being delivered into tissue. The at least 50% of the injectate can remain in the therapeutic restriction at least three months after being delivered into tissue. The at least 50% of the injectate can remain in the therapeutic restriction at least six months after being delivered into tissue. The at least 50% of the injectate can remain in the therapeutic restriction at least one year after being delivered into tissue.

In some embodiments, the injectate comprises ethylene vinyl alcohol (EVOH). The injectate can further comprise dimethyl sulfoxide. The injectate can further comprise a second material constructed and arranged to polymerize the ethylene vinyl alcohol. The delivery element can comprise a first delivery element that delivers the ethylene vinyl alcohol and a second delivery element that delivers the second material. The injectate can further comprise saline. The delivery element can comprise a first delivery element that delivers the ethylene vinyl alcohol and a second delivery element that delivers the saline.

In some embodiments, the injectate comprises a peptide polymer.

In some embodiments, the injectate comprises polylactic acid.

In some embodiments, the injectate comprises polymethylmethacrylate.

In some embodiments, the injectate comprises a hydrogel. The hydrogel can be constructed and arranged to expand after delivery into tissue.

In some embodiments, the injectate comprises material harvested from a mammalian body. The method can further comprise harvesting the material from the mammalian body. The injectate can comprise autologous material. The injectate can comprise material selected from the group consisting of: fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; and combinations thereof. The injectate can comprise a peptide polymer configured to stimulate fibroblasts to produce collagen.

In some embodiments, the injectate comprises a sclerosant.

In some embodiments, the injectate comprises an adhesive. The injectate can comprise cyanoacrylate.

In some embodiments, the injectate is constructed and arranged to expand after delivery into tissue.

In some embodiments, the injectate comprises an agent configured to elute into tissue over time. The agent can comprise a pharmaceutical agent.

In some embodiments, the injectate comprises a radiopaque material.

In some embodiments, the injectate comprises a visible dye.

In some embodiments, the injectate comprises an ultrasonically reflective material.

In some embodiments, the injectate comprises a first material and a second material. The first material and the second material can be delivered into tissue simultaneously. The delivery element can comprise a first delivery element and a second delivery element, and the first material can be delivered by the first delivery element and the second material can be delivered by the second delivery element. In these embodiments, the first delivery element can comprise a first lumen of a needle and the second delivery element can comprise a second lumen of the same needle. Alternatively, the first delivery element can comprise a first needle or other first fluid delivery element and the second delivery element can comprise a second, separate needle or other second fluid delivery element. The first material and/or the second material can undergo at least one of a chemical change or a physical change, such as when the first material and the second material are brought into contact with each other. The first material and the second material can be brought into contact with each other when positioned in tissue. The first material and the second material can form a hydrogel. The first material and the second material can form a material with increased viscosity when brought into contact with each other. The first material can polymerize when brought into contact with the second material.

In some embodiments, the injectate is constructed and arranged to polymerize when delivered into tissue.

In some embodiments, the delivery element is advanced endoscopically.

In some embodiments, the delivery element is advanced to the location proximate the luminal segment via a lumen of the gastrointestinal tract.

In some embodiments, the delivery element is advanced to the location proximate the luminal segment via space outside the gastrointestinal tract. The delivery element can be advanced through a laparoscopic probe.

In some embodiments, the delivery element comprises one or more elements selected from the group consisting of: a needle; a fluid jet; an iontophoretic element; and combinations thereof.

In some embodiments, the delivery element comprises at least one needle with a diameter of at least 30 gauge (e.g. 30 gauge, 29 gauge or bigger). The delivery element can comprise at least one needle with a diameter of at least 27 gauge. The delivery element can comprise a diameter of at least 23 gauge.

In some embodiments, the delivery element comprises a diameter less than 20 gauge (e.g. 20 gauge, 21 gauge or smaller).

In some embodiments, the delivery element comprises multiple delivery elements positioned on an expandable element such as a balloon. The multiple delivery elements can be circumferentially spaced, such as in a circumferential array positioned on a balloon or other expandable element. The multiple delivery elements can be spaced at relatively equal distances. In some embodiments, multiple delivery elements are included in a single structure, such as a single needle with multiple lumens.

In some embodiments, the method further comprises providing a seal around the delivery element, such as a seal provided by an O-ring.

In some embodiments, the method further comprises applying heat to the injectate. The heat can be applied prior to delivery of the injectate into tissue. The injectate can be delivered at a temperature below a threshold that would cause damage to the muscularis layer of the gastrointestinal tract. The delivery element can be positioned on a shaft with a lumen and the injectate can be heated while in the lumen of the shaft. The delivery element can be positioned on a shaft with a lumen and the injectate can be heated prior to being introduced into the lumen of the shaft.

In some embodiments, the method further comprises applying a vacuum to tissue at least one of prior to or during the delivery of the injectate.

In some embodiments, the method further comprises performing a luminal sizing procedure to produce luminal diameter data, luminal geometry data and/or other luminal data. The luminal sizing procedure can be performed prior to delivery of the injectate to determine an amount of injectate to be delivered. The luminal sizing procedure can be performed during delivery of the injectate. The luminal sizing procedure can be performed to monitor a therapeutic restriction parameter, such as to monitor the inner diameter of the therapeutic restriction such as to deliver the injectate in a closed-loop manner. The luminal data can be used to perform a function selected from the group consisting of: sizing of an expandable assembly; determining a volume of the injectate to be delivered; determining a composition of the injectate to be delivered; determining a therapeutic restriction parameter such as inner diameter, pressure and/or volume; determining the pressure required to advance a sizing device through the GI tract beyond the therapeutic restriction; and combinations thereof.

In some embodiments, the method further comprises performing at least a second therapeutic procedure. The second therapeutic procedure can be constructed and arranged to improve the therapeutic result of the first procedure. The improved therapeutic results can be selected from the group consisting of: improved anti-diabetic effect; improved anti-obesity effect; and combinations thereof. The second procedure can be performed within two years of the first procedure. The second procedure can be performed within one year of the first procedure. The second procedure can be performed within one month of the first procedure. The second procedure can be performed within one week of the first procedure. The second therapeutic procedure can create a second therapeutic restriction and/or it can increase the volume of and/or otherwise modify the first therapeutic restriction. Alternatively or additionally, the second therapeutic procedure can cause a modification of mucosal tissue selected from the group consisting of: a reduction in mucosal surface area; mucosal regrowth; a change in mucosal absorption properties; a change in mucosal secretion properties; and combinations thereof. The mucosal tissue can comprise small intestine mucosal tissue. The mucosal tissue can comprise duodenal mucosal tissue.

In some embodiments, the method further comprises advancing the delivery element through and/or alongside a body introduction device. The body introduction device can comprise an endoscope, a sheath for attachment to the endoscope and/or a laparoscopic probe.

According to another aspect of the present invention, a system for treating a patient comprises a delivery device and an injectate. The delivery device can further comprise an elongate shaft with a distal portion. The delivery device can further comprise at least one delivery element positioned on the elongate shaft distal portion. The delivery device can be constructed and arranged to deliver the injectate through the at least one delivery element and into tissue to create a therapeutic restriction in the gastrointestinal tract. The delivery device can further comprise a guidewire lumen, such as to support over-the-wire delivery of the delivery device into the GI tract of the patient.

In some embodiments, the therapeutic restriction is positioned in a luminal segment of the gastrointestinal tract.

In some embodiments, the therapeutic restriction is positioned in the stomach.

In some embodiments, the system is constructed and arranged to create a second therapeutic restriction in a lumen of a second segment of the GI tract and/or to increase the volume of the first therapeutic restriction.

In some embodiments, the at least one delivery element comprises at least two delivery elements. The at least one delivery element can comprise at least three delivery elements. The injectate can comprise a first material and a second material and the at least two fluid delivery elements can be constructed and arranged to prevent mixing of the first material and the second material prior to delivery into tissue. In some embodiments, two or more delivery elements are included in a single structure, such as a single needle with multiple lumens.

In some embodiments, the delivery element is constructed and arranged to be advanced through and/or alongside an endoscope, and/or through a sheath attached to the endoscope.

In some embodiments, the delivery element is constructed and arranged to be advanced to the location proximate the luminal segment via the gastrointestinal tract.

In some embodiments, the delivery element is constructed and arranged to be advanced to the location proximate the luminal segment via space outside the gastrointestinal tract. The system can further comprise a laparoscopic probe, and the delivery element can be constructed and arranged to be advanced through the laparoscopic probe.

In some embodiments, the delivery element comprises one or more elements selected from the group consisting of: a needle; a fluid jet; an iontophoretic element; and combinations thereof.

In some embodiments, the delivery element comprises at least one needle with a diameter of at least 30 gauge. The delivery element can comprise at least one needle with a diameter of at least 27 gauge. The delivery element can comprise a diameter of at least 23 gauge.

In some embodiments, the delivery element comprises a diameter less than 20 gauge.

In some embodiments, the delivery element comprises multiple delivery elements positioned on an expandable element such as a balloon. The multiple delivery elements can be circumferentially spaced, such as in a circumferential array positioned on a balloon or other expandable element. The multiple delivery elements can be spaced at relatively equal distances.

In some embodiments, the system further comprises a sealing element around the at least one delivery element. The sealing element can comprise an O-ring.

In some embodiments, the delivery device comprises at least one vacuum port surrounding the at least one delivery element.

In some embodiments, the injectate comprises an amount (e.g. volume or mass) of material that is selected or otherwise determined based on a patient parameter. The patient parameter can be selected from the group consisting of: body weight; body mass index; excess weight based on established norms; age; HbA1c level; cholesterol level; and combinations thereof.

In some embodiments, the injectate comprises an amount of material determined prior to delivery of the injectate into tissue.

In some embodiments, the injectate comprises an amount of material determined during delivery of the injectate into tissue. The amount of material can be determined based on a parameter selected from the group consisting of: pressure within the therapeutic restriction; pressure within tissue proximate the therapeutic restriction; volume of the therapeutic restriction; diameter of the therapeutic restriction; and combinations thereof.

In some embodiments, the system is constructed and arranged to create a therapeutic restriction comprising a volume that decreases over time. The injectate can comprise a first material and a second material, and the second material can be constructed and arranged to remain in the therapeutic restriction for a longer time period than the first material, and the second material can be delivered at least one day after the first material is delivered.

In some embodiments, at least 50% of the injectate remains in the therapeutic restriction at least one month after being delivered into tissue. The at least 50% of the injectate can remain in the therapeutic restriction at least three months after being delivered into tissue. The at least 50% of the injectate can remain in the therapeutic restriction at least six months after being delivered into tissue. The at least 50% of the injectate can remain in the therapeutic restriction at least one year after being delivered into tissue.

In some embodiments, the injectate comprises ethylene vinyl alcohol. The injectate can further comprise dimethyl sulfoxide. The injectate can further comprise a second material constructed and arranged to polymerize the ethylene vinyl alcohol. The delivery element can comprise a first delivery element that delivers the ethylene vinyl alcohol and a second delivery element that delivers the second material. The injectate can further comprise saline. The delivery element can comprise a first delivery element that delivers the ethylene vinyl alcohol and a second delivery element that delivers the saline.

In some embodiments, the injectate comprises a peptide polymer.

In some embodiments, the injectate comprises polylactic acid.

In some embodiments, the injectate comprises polymethylmethacrylate.

In some embodiments, the injectate comprises a hydrogel. The hydrogel can be constructed and arranged to expand after delivery into tissue.

In some embodiments, the injectate comprises material harvested from a mammalian body. The system can further comprise harvesting the material from the mammalian body. The injectate can comprise autologous material. The injectate can comprise material selected from the group consisting of: fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; and combinations thereof. The injectate can comprise a peptide polymer configured to stimulate fibroblasts to produce collagen.

In some embodiments, the injectate comprises a sclerosant.

In some embodiments, the injectate comprises an adhesive. The injectate can comprise cyanoacrylate.

In some embodiments, the injectate is constructed and arranged to expand after delivery into tissue.

In some embodiments, the injectate comprises an agent configured to elute into tissue over time. The agent can comprise a pharmaceutical agent.

In some embodiments, the injectate comprises a radiopaque material.

In some embodiments, the injectate comprises a visible dye.

In some embodiments, the injectate comprises an ultrasonically reflective material.

In some embodiments, the injectate comprises a first material and a second material. The first material and the second material can be delivered into tissue simultaneously. The delivery element can comprise a first delivery element and a second delivery element, and the first material can be delivered by the first delivery element and the second material can be delivered by the second delivery element. The first material and the second material can undergo at least one of a chemical change or a physical change when brought into contact with each other. The first material and the second material can be brought into contact with each other in tissue. The first material and the second material can form a hydrogel. The first material and the second material can form a material with increased viscosity when brought into contact with each other. The first material can polymerize when brought into contact with the second material.

In some embodiments, the injectate is constructed and arranged to polymerize when delivered into tissue.

In some embodiments, the system further comprises an endoscope and/or a sheath constructed and arranged to be attached to the endoscope. The delivery device can be constructed and arranged to be slidingly advanced through the endoscope and/or through a sheath attached to the endoscope. Alternatively, the delivery device can be constructed and arranged to advance alongside an endoscope, such as during delivery over a guidewire.

In some embodiments, the system further comprises a laparoscopic probe. The delivery device can be constructed and arranged to be slidingly advanced through the laparoscopic probe.

In some embodiments, the system further comprises a luminal sizing element. The luminal sizing element can comprise an expandable element positioned on the shaft. Alternatively, the luminal sizing element can comprise an expandable element positioned on a separate sizing device.

In some embodiments, the system further comprises an algorithm configured to determine a therapeutic restriction parameter. The therapeutic restriction parameter determined by the algorithm can comprise the amount (e.g. volume and/or mass) of injectate to be delivered to create the therapeutic restriction. The therapeutic restriction parameter determined by the algorithm can comprise a dimensional parameter of the therapeutic restriction.

In some embodiments, the system further comprises a heating element constructed and arranged to apply heat to the injectate. The heating element can be positioned in the shaft. The heating element can be positioned external to the shaft. The heating element can be constructed and arranged to heat the injectate to a temperature below a threshold that would cause damage to tissue of a muscularis layer of the gastrointestinal tract.

According to another aspect of the present invention, a method for treating a patient comprises advancing a delivery element to a location of the gastrointestinal tract of the patient and delivering an injectate through the delivery element and into tissue to create a therapeutic restriction in the gastrointestinal tract.

In some embodiments, the therapeutic restriction is positioned in the stomach.

In some embodiments, the therapeutic restriction is positioned in a luminal segment of the gastrointestinal tract.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIGS. 3A-3D are four sets of side and end sectional views of various therapeutic restriction configurations, consistent with the present inventive concepts.

FIG. 7A is a sectional view of the stomach of FIG. 7 including a series of therapeutic restrictions along the majority of a circumference of the stomach, consistent with the present inventive concepts.

FIG. 7B is a sectional view of the stomach of FIG. 7 including one or more therapeutic restrictions along a partial circumference of the stomach, consistent with the present inventive concepts.

FIGS. 11A-11D are a series of side and end sectional views of a segment of the gastrointestinal tract, prior to creation of a therapeutic restriction, after creation of a therapeutic restriction, after a time period in which the therapeutic restriction has partially decreased, and after a time period in which the therapeutic restriction has fully reduced, respectively, consistent with the present inventive concepts.

DETAILED DESCRIPTION OF THE INVENTION

Figure 1:
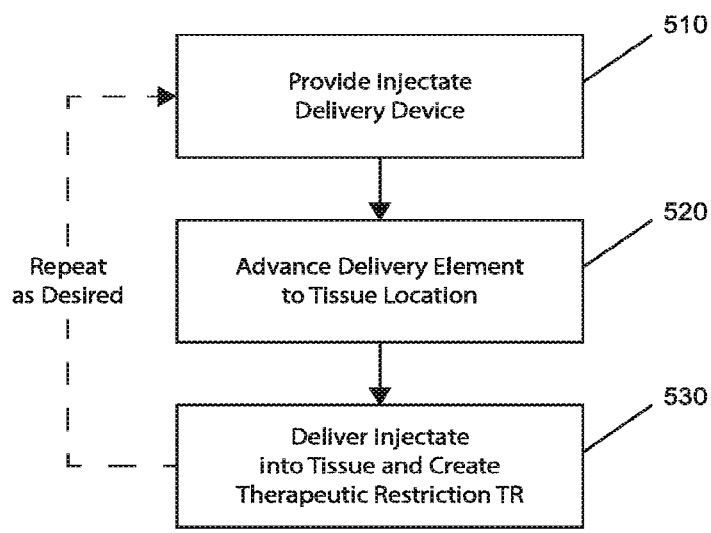
FIG. 1 is a flow chart of a method for creating a therapeutic restriction within the gastrointestinal tract of a patient, consistent with the present inventive concepts.

The terminology used herein is for the purpose of describing particular embodiments and is not intended to be limiting of the inventive concepts. Furthermore, embodiments of the present inventive concepts may include several novel features, no single one of which is solely responsible for its desirable attributes or which is essential to practicing an inventive concept described herein. As used herein, the singular forms "a," "an" and "the" are intended to include the plural forms as well, unless the context clearly indicates otherwise.

It will be further understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element or intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

Spatially relative terms, such as "beneath," "below," "lower," "above," "upper" and the like may be used to describe an element and/or feature's relationship to another element(s) and/or feature(s) as, for example, illustrated in the figures. It will be understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g., rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

As described herein, room pressure shall mean pressure of the environment surrounding the systems and devices of the present inventive concepts. Positive pressure includes pressure above room pressure or a pressure that is greater than another pressure, such as a positive differential pressure across a fluid pathway component such as a valve. Negative pressure includes pressure below room pressure or a pressure that is less than another pressure, such as a negative differential pressure across a fluid component pathway such as a valve. Negative pressure can include a vacuum but does not imply a pressure below a vacuum. As used herein, the term "vacuum" can be used to refer to a full or partial vacuum, or any negative pressure as described hereabove.

The term "diameter" where used herein to describe a non-circular geometry is to be taken as the diameter of a hypothetical circle approximating the geometry being described. For example, when describing a cross section, such as the cross section of a component, the term "diameter" or shall be taken to represent the diameter of a hypothetical circle with the same cross sectional area as the cross section of the component being described.

Systems, devices and methods of the present inventive concepts create a therapeutic restriction, such as a luminal narrowing of one or more gastrointestinal (GI) segments and/or a reduction in a volume of a GI space (e.g. reduction in volume of the stomach). One or more delivery elements deliver an injectate comprising one or more materials into tissue, such as gastrointestinal (GI) tissue, to create the therapeutic restriction.

Referring now to FIG. 1, a flow chart of a method for creating a therapeutic restriction in a patient is illustrated, consistent with the present inventive concepts. In STEP 510, an injectate delivery device is provided. A system for providing injectate to the delivery device can also be provided. The injectate delivery device and/or system can be similar to device 100 and/or system 10 described herebelow in reference to FIG. 2. In some embodiments, the injectate delivery device provided can be similar to the tissue expansion device described in applicant's co-pending U.S. patent application Ser. No. 14/515,324, entitled "Tissue Expansion Device, Systems and Methods", filed Oct. 15, 2014, the contents of which is incorporated herein by reference in its entirety.

In STEP 520, one or more delivery elements of the injectate delivery device are advanced to a tissue location of a patient, such as a location proximate a luminal segment of the GI tract. The injectate device delivery elements can be first advanced through an introduction device such as an endoscope (and/or a sheath attached to an endoscope) that has been placed through the mouth of the patient to an internal body location such as the stomach, duodenum or jejunum. In some embodiments, the injectate delivery device is advanced through the anus of the patient, such as to an internal body location such as the anal sphincter, rectum or colon. In some embodiments, the injectate delivery element is advanced through a laparoscopic probe, such as a laparoscopic probe providing entry into the stomach or small intestine.

In STEP 530, injectate is delivered into target tissue (e.g. tissue proximate the luminal segment) through one or more delivery elements of the injectate delivery device. In some embodiments, the one or more delivery elements are mounted to an expandable element such as a balloon which is expanded prior to the delivery of the injectate. The target tissue can comprise a continuous volume of tissue or multiple discrete volumes of tissue. In some embodiments, injectate is delivered into target tissue by two or more delivery elements positioned proximate to and along a circumference of the GI tract. In some embodiments, between 1.0 mL and 10.0 mL of fluid is delivered per delivery element, such as between 1.0 mL and 4.0 mL of fluid per delivery element. In some embodiments, a therapeutic restriction with a circumferential and/or linear geometry is created, wherein between 3.0 mL and 20 mL are delivered, such as between 4.0 mL and 8.0 mL of fluid injected to create the therapeutic restriction. In some embodiments, one or more parameters are measured during delivery of the injectate, such as diameter of a lumen volume, pressure within tissue receiving the injectate and/or pressure of the injectate being delivered (e.g. to perform a closed-loop creation of the therapeutic restriction).

In some embodiments, prior to injectate delivery, a vacuum is applied to one or more ports of the injectate delivery device (e.g. one or more ports proximate a fluid delivery element such as one or more ports on an expandable assembly such as a balloon) to cause tissue such as stomach wall tissue or small intestine luminal wall tissue to be in close proximity to the one or more fluid delivery elements. In some embodiments, at least one fluid delivery element comprises a fluid jet configured to deliver the injectate in a manner to penetrate the surface of tissue. In some embodiments, at least one delivery element comprises an iontophoretic element configured to deliver injectate into fluid using electromagnetic fields. In some embodiments, at least one delivery element comprises a needle which is advanced through a tissue surface prior to delivery of the injectate to target tissue. The needle can comprise one or more lumens, such as a needle comprising multiple lumens which can deliver different injectates without mixing prior to their delivery into tissue. Delivery of injectate into target tissue causes a therapeutic restriction TR to be formed within a GI tract segment or other GI tract location of the patient. The therapeutic restriction TR can comprise a luminal restriction or other cross sectional area restriction (hereinafter luminal restriction) with various sizes and geometries, such as are described herebelow in reference to FIGS. 3A-3D. The therapeutic restriction TR can be positioned in one or more anatomical locations as described herein, such as are described herebelow in reference to FIGS. 4-10.

The injectate delivered to create the therapeutic restriction TR can be constructed and arranged such that the volume of the therapeutic restriction TR decreases over time, such as when the injectate is absorbed, degrades, migrates and/or otherwise is reduced from within the therapeutic restriction TR over time, such as is described herebelow in reference to FIGS. 2, 3A-3D and 11A-11D.

In some embodiments, one or more therapeutic restrictions TR comprise a therapeutic restriction parameter, such as a dimensional parameter, that is based on a patient parameter, such a measured patient parameter. In these embodiments, the therapeutic restriction parameter can comprise a dimensional parameter selected from the group consisting of: volume; axial length; arc length (e.g. between 15° and 360°); surface area; and combinations of these. In these embodiments, the patient parameter can comprise a parameter selected from the group consisting of: body weight; body mass index; excess weight based on established norms; age; HbA1c level; cholesterol level; blood pressure; and combinations of these.

One or more therapeutic restrictions TR of the present inventive concepts can be created at a location (e.g. the location of the target tissue receiving injectate delivery) selected from the group consisting of: within mucosal tissue; within submucosal tissue; between mucosal and submucosal tissue; and combinations of these. One or more therapeutic restrictions TR can be created at a location selected from the group consisting of: lower stomach; pylorus; proximal small intestine (e.g. the duodenum and/or proximal jejunum); distal small intestine (e.g. the distal jejunum and/or ileum); colon; rectum; anal sphincter and combinations of these.

Figure 2:
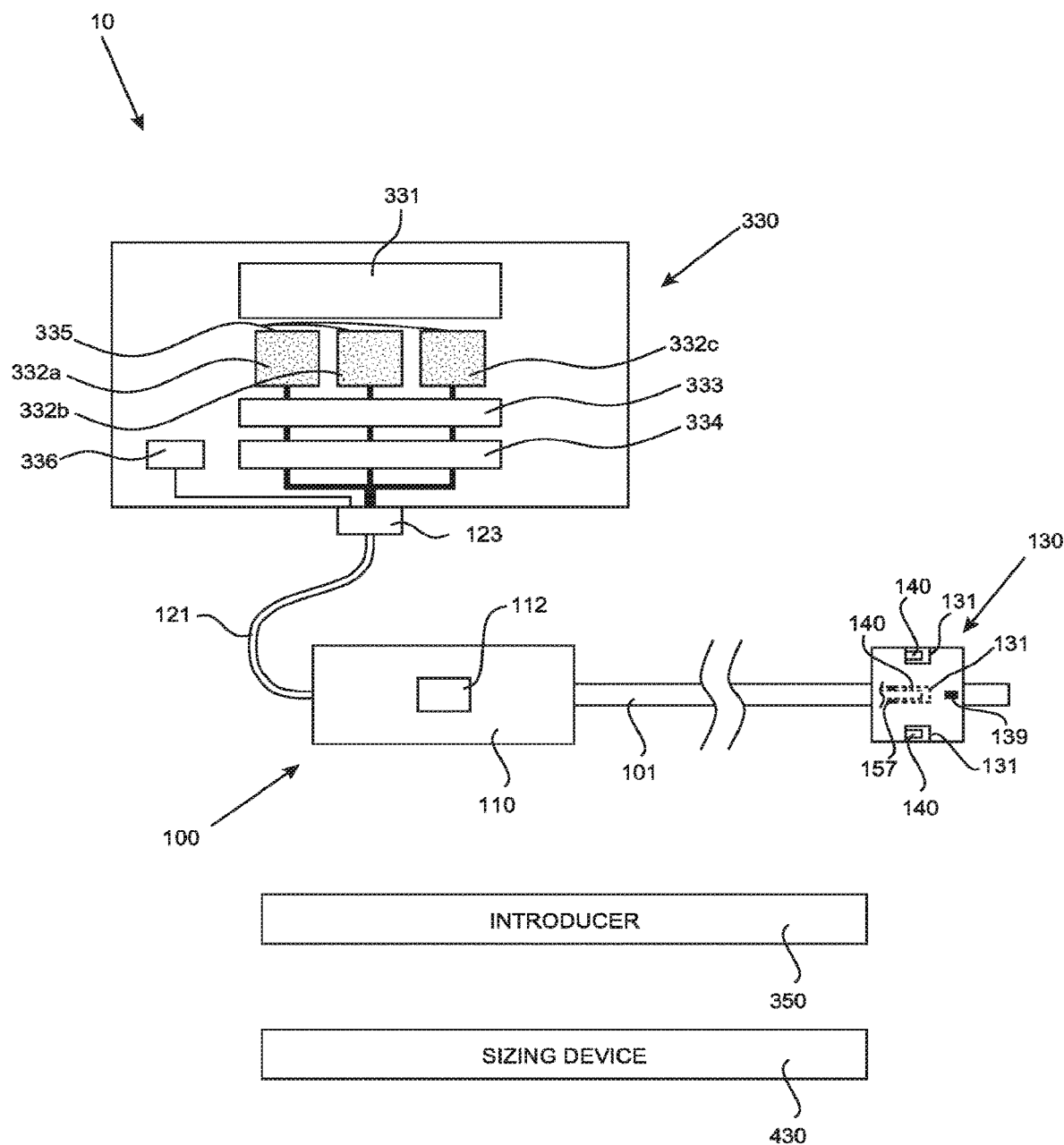
FIG. 2 is a schematic view of a system for creating a therapeutic restriction within the gastrointestinal tract of a patient, consistent with the present inventive concepts.

The systems, devices and methods of the present inventive concepts, such as those described in reference to STEPs 510 through 530 of FIG. 1 and system 10 of FIG. 2, can be performed to treat a patient or disease or disorder, such as a patient disease or disorder selected from the group consisting of: obesity; type 2 diabetes; type 1 diabetes; hypercholesterolemia; hypertension; metabolic disease; a metabolic syndrome; and combinations thereof, such as when one or more therapeutic restrictions TR of the present inventive concepts can be created at an anatomical location selected from the group consisting of: lower stomach; pylorus; proximal small intestine; duodenum; proximal jejunum; distal small intestine; distal jejunum; ileum; and combinations of these. One or more therapeutic restrictions TR can be configured to restrict a passage of food through a portion of the GI tract. One or more therapeutic restrictions TR can be configured to cause one or more of: early satiety; premature satiety; or satiety. The systems, devices and methods of the present inventive concepts can be constructed and arranged to alter an absorptive property and/or a secretive property of the patient's gastrointestinal tract. Alternatively or additionally, the systems, devices and methods of the present inventive concepts can be constructed and arranged to alter hormonal signaling of the patient. In some embodiments, one or more therapeutic restrictions TR are created to treat fecal incontinence, such as when at least one therapeutic restriction TR is created in the colon, rectum and/or anal sphincter.

The injectate can be delivered in one or more injections, in one or more tissue locations proximate the therapeutic restriction TR to be created. Delivery of the injectate can be based (e.g. amount of injectate delivered and/or location of injectate delivery) on one or more patient parameters, such as one or more parameters selected from the group consisting of: body weight; body mass index; excess weight based on established norms; age; HbA1c level; cholesterol level; and combinations of these. Alternatively, delivery of the injectate can be based (e.g. amount of injectate delivered and/or location of injectate delivery) on a therapeutic restriction parameter and/or a therapeutic restriction location parameter selected from the group consisting of: pressure within the therapeutic restriction; pressure within tissue proximate the therapeutic restriction; volume of the therapeutic restriction; diameter of the therapeutic restriction; and combinations thereof. The amount of injectate delivered (e.g. volume or mass) can be determined prior to and/or during the clinical procedure creating the therapeutic restriction TR, such as by measuring one or more patient parameters or therapeutic restriction parameters during delivery of the injectate.

In some embodiments, the injectate comprises material harvested from a mammalian body, and one or more of STEPs 510 through 530 can include harvesting the injectate, such as when the injectate comprises material harvested from the patient (i.e. autologous material), or material harvested from another mammalian subject. In these embodiments, the injectate can comprise a material selected from the group consisting of: fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; and combinations of these. The injectate can comprise a peptide polymer configured to stimulate fibroblasts, such as to produce collagen.

In some embodiments, STEPs 510 through 530 are repeated, such as during the same clinical procedure (e.g. on the same day), to create a second therapeutic restriction TR2 (hereinafter "TR") formed within a different GI tract location of the patient. In some embodiments, a second therapeutic restriction TR is formed in a second clinical procedure performed at least 24 hours from the first clinical procedure, such as at least 1 week, 1 month, 3 months or 6 months after the creation of the first therapeutic restriction TR. In some embodiments, three or more therapeutic restrictions are created in one or more clinical procedures. A first therapeutic restriction TR and a second therapeutic restriction TR can be separated by a linear distance (e.g. a distance along the central axis of the small intestine) of at least 5 mm, such as a separation of at least 10 mm. In some embodiments, STEPs 510 through 530 are repeated to increase the volume of the first therapeutic restriction TR, with or without the creation of a second therapeutic restriction TR.

A second therapeutic restriction TR can be similar or dissimilar to a first therapeutic restriction TR, such as a therapeutic restriction created using similar or dissimilar injectate materials, injectate volumes delivered, injectate delivery devices, injectate delivery systems, and/or injectate delivery methods. A second therapeutic restriction TR can comprise similar or dissimilar shapes or dimensions than the first therapeutic restriction TR.

A second therapeutic restriction TR can comprise a boundary that is positioned at least 1 mm from the most proximate boundary of the first therapeutic restriction TR, such as two corresponding boundaries that are positioned at least 5 mm apart and/or within 100 mm from each other.

A second therapeutic restriction TR can be created based on a patient parameter selected from the group consisting of: body weight; body mass index; excess weight based on established norms; age; HbA1c level; cholesterol level; and combinations of these. A second therapeutic restriction TR can be created based on a patient parameter tending toward an undesired level, such as patient weight increasing to an undesired level after the creation of a first therapeutic restriction TR.

The method of the present inventive concepts can include performing a second therapeutic procedure on the patient, such as the creation of a second therapeutic restriction TR as described hereabove, or a different therapeutic procedure. In some embodiments, a dissimilar second procedure is performed, prior to or after the procedure creating the therapeutic restriction TR. A second therapeutic procedure can be configured to improve the therapeutic result of the therapeutic restriction TR, such as to improve an anti-diabetic effect and/or an anti-obesity effect. The creation of the therapeutic restriction TR and a second therapeutic procedure can be performed within 2 years of each other, such as within 1 year, 1 month or 1 week of each other. In some embodiments, a second therapeutic procedure is configured to reduce the mucosal surface area (e.g. the small intestine mucosa such as the duodenal mucosa) or otherwise treat the patient as described in applicant's co-pending International Patent Application Serial Number PCT/US2014/040957, entitled "Methods, Systems and Devices for Reducing the Luminal Surface Area of the Gastrointestinal Tract", filed Jun. 4, 2014, the contents of which is incorporated herein by reference in its entirety. In some embodiments, the patient's diet is altered, prior to and/or after the creation of one or more therapeutic restrictions, such as a diet with reduced fat and/or reduced caloric intake.

Referring now to FIG. 2, a schematic view of a system for creating a therapeutic restriction within the GI tract of a patient is illustrated, consistent with the present inventive concepts. System 10 includes an injectate delivery device 100 constructed and arranged to deliver an injectate to target tissue to create a therapeutic restriction. In some embodiments, system 10 and/or device 100 can be of similar construction and arrangement to the tissue expansion systems and devices described in applicant's co-pending U.S. patent application Ser. No. 14/515,324, entitled "Tissue Expansion Device, Systems and Methods", filed Oct. 15, 2014, the contents of which is incorporated herein by reference in its entirety. System 10 can further include injectate delivery unit (IDU) 330 constructed and arranged to provide one or more injectable materials, such as first injectate 332a, second injectate 332b and/or third injectate 332c (singly or collectively "injectate 332") to device 100. System 10 can further include a body introduction device, introducer 350, such as an endoscope, a sheath for attachment to an endoscope, a guidewire, a laparoscopic probe and/or other device used to advance one or more delivery elements 140 and/or another portion of device 100 to an internal body location such as the stomach, upper intestine or lower intestine. In some embodiments, a distal portion of device 100 including one or more delivery elements 140 is advanced through one or more working channels of introducer 350. In some embodiments, one or more delivery elements 140 are advanced to a location within a lumen of a segment of the GI tract, such as to deliver injectate 332 to target tissue comprising GI submucosa or other GI tissue from a location within a segment of the GI tract (e.g. injectate delivered through an inner wall of the GI tract). In other embodiments, one or more delivery elements 140 are advanced to a location outside of a segment of the GI tract (e.g. outside of the serosal layer such as via a laparoscopic probe), such as to deliver injectate 332 to target tissue comprising GI submucosa or other GI tissue from a location outside of the GI tract (e.g. injectate delivered through an outer wall of the GI tract).

Injectate 332 can comprise one or more materials used to expand one or more layers of tissue and/or occupy volume within one or more layers of tissue to narrow a lumen of a GI segment or otherwise reduce volume of a GI space (e.g. reduce the space within the stomach). Injectate 332 can be constructed and arranged such that at least 50% of the volume injected remains in the therapeutic restriction after a time period has elapsed (e.g. the remainder has been absorbed, evacuated from the patient and/or migrated within the patient to another body location outside of the therapeutic restriction), such as a time period of at least 1 month, 3 months, 6 months or 1 year.

Injectate delivery device 100 can comprise a handle 110 and an attached elongate shaft, shaft 101. Shaft 101 can be of sufficient rigidity and flexibility to navigate one or more portions of the patient's anatomy. In some embodiments, shaft 101 is constructed and arranged for over-the-wire delivery (e.g. includes one or more guidewire lumens or a distal segment comprising a rapid exchange guidewire sidecar). An expandable assembly 130 can be positioned on a distal portion of shaft 101 (expandable assembly 130 shown in FIG. 1 in its radially expanded state). Expandable assembly 130 can comprise an expandable balloon, expandable cage or an array of radially deployable arms. Positioned on, in or within expandable assembly 130 are one or more delivery elements 140, such as the three delivery elements 140 shown in FIG. 2. Multiple delivery elements 140 can be positioned about a circumference of expandable assembly 130, such as two or more delivery elements 140 equally spaced about the circumference (e.g. equally spaced about a circumference that lies in a plane relatively orthogonal to shaft 101). Delivery elements 140 can comprise one or more delivery elements selected from the group consisting of: needle; fluid jet; iontophoretic fluid delivery element; and combinations of these. In some embodiments, one or more delivery elements 140 comprise a needle with a diameter of at least 30 gauge, such as a diameter of at least 27 gauge or at least 23 gauge. In some embodiments, one or more delivery elements 140 comprise a needle with a diameter less than 20 gauge. In some embodiments, one or more delivery elements 140 comprise a needle with multiple lumens.

In some embodiments, device 100 comprises a sealing element 157 configured to provide a seal around one or more delivery elements 140, such as an O-ring surrounding the shaft of a needle. Sealing element 157 can be constructed and arranged to allow a needle or other delivery element 140 to slidingly advance through sealing element 157 while preventing injectate 332 or other fluid to pass between sealing element 157 and delivery element 140 such as to prevent clogging of a vacuum lumen and/or other lumen of shaft 101.

In some embodiments, device 100 comprises multiple delivery elements 140, such as multiple needles. In these embodiments, the multiple delivery elements 140 can be circumferentially spaced about a balloon or other expandable assembly such as expandable assembly 130. The multiple delivery elements 140 can be spaced apart at relatively equal distances, such as three delivery elements separated by 120° along a circumference of expandable assembly 130.

Device 100 can include tube assembly 121 which terminates in fluid connector 123, such that injectate 332 and/or one or more other fluids can be delivered into one or more lumens of tube assembly 121, and pass through one or more lumens of handle 110 and shaft 101 to delivery elements 140. In some embodiments, fluid connector 123 can also operably connect one or more non-fluid delivery conduits between device 100 and IDU 330, such as one or more wires, optical fibers or other flexible conduits.

As shown in FIG. 2, connector 123 has been operably attached to IDU 330, such that injectate 332 can be provided to device 100. IDU 330 can include one or more injectates 332 (three shown in FIG. 2) contained within one or more reservoirs 335 (three shown in FIG. 2). Reservoirs 335 can be operably connected (e.g. in fluid communication with) one or more heaters 333 (one shown in FIG. 2, e.g. a single heater with multiple fluid pathways configured to prevent mixing of multiple injectates 332 if desired). In some embodiments, IDU 330 comprises multiple injectates 332 (e.g. injectates 332a, 332b and 332c shown) and a subset of injectates 332 are heated by heater 333 and a subset are not heated by heater 333. One or more injectates 332 can be heated by heater 333 prior to delivery into tissue.

IDU 330 can further comprise one or more pumping assemblies 334 constructed and arranged to propel one or more injectates 332 into device 100 and/or out of delivery elements 140. Pumping assemblies 334 can comprise a source of pressure (e.g. a source of pressure applied to one or more reservoirs 335) and/or a pumping element such as an element selected from the group consisting of: magneto hydrodynamic fluid propulsion element; centrifugal pump; peristaltic pump; syringe pump; and combinations of these. Heater 333 and/or pumping assembly 334 can be configured to prevent mixing and/or cause mixing of one or more of injectate 332a, 332b and/or 332c.

IDU 330 can further comprise a user interface 331, such as a user interface including one or more user input and/or user output components selected from the group consisting of: touch screen; keyboard; mouse; visual display; speaker; microphone; and combinations of these. User interface 331 can be used to initiate, cease and/or modify injectate 332 delivery, such as to modify one or more of: temperature of injectate 332; flow rate of injectate 332; pressure of injectate 332; and an alarm threshold of injectate 332 delivery.

Device 100 can comprise one or more openings or ports, openings 131, positioned proximate each delivery element 140. The one or more openings 131 can be constructed and arranged to apply a vacuum, such as to bring tissue in close proximity to each fluid delivery element 140. In some embodiments, IDU 330 is constructed and arranged to controllably provide a vacuum to openings 131, such as via one or more lumens within shaft 101 configured to maintain a vacuum. The one or more openings 131 can be sized to allow tissue to enter opening 131, allowing the associated delivery element 140 to penetrate or otherwise deliver fluid into the captured tissue without delivery element 140 exiting opening 131 (e.g. without a delivery element 140 comprising a needle exiting opening 131).

A control 112, shown positioned on handle 110, can comprise one or more elements constructed and arranged to initiate or otherwise control the delivery of injectate 332 to target tissue. In some embodiments, control 112 is configured to control a vacuum applied to one or more openings 131. In some embodiments, control 112 is configured to advance one or more delivery elements 140, such as to sequentially or simultaneously advance one or more delivery elements 140 comprising a needle. In some embodiments, control 112 is constructed and arranged to provide one or more control signals to IDU 330. Control 112 can comprise a pumping assembly, a mechanical and/or electrical switch, an advanceable slide; a rotatable knob; a cam mechanism; a valve or valve controller; and combinations of these.

Device 100 can include one or more functional elements, such as functional element 139. Functional element 139 is shown in FIG. 2 positioned on, in and/or within expandable assembly 130. Alternatively or additionally, one or more functional elements 139 can be positioned on, in or within shaft 101 and/or handle 110. Functional element 139 can comprise a sensor and/or a transducer. In some embodiments, functional element 139 comprises one or more sensors selected from the group consisting of: temperature sensor; pressure sensor; strain gauge; optical sensor; magnetic sensor; electrical sensor; electrode; and combinations of these. Alternatively or additionally, functional element 139 can comprise one or more transducers selected from the group consisting of: a fluid stirring and/or agitating element; a heating element; a cooling element; a piezo crystal; a sound transducer; an electromagnetic transducer; and combinations of these. In some embodiments, functional element 139 comprises a heating element constructed and arranged to heat one or more injectates 332. In some embodiments, IDU 330 comprises a source of power, source 336, which can supply energy to one or more components of device 100 (e.g. via connector 123), such as to supply power to functional element 139 such as when functional element 139 comprises a heating element. Alternatively or additionally, source 336 can be configured as a vacuum source, such as to supply a vacuum about opening 131 of device 100 as described hereabove, such as to position tissue within and/or proximate opening 131 and/or delivery element 140.

In some embodiments, injectate 332 comprises a single material, or one or more materials selected from the group consisting of: a gas; a liquid; a gel; and combinations of these. In other embodiments, injectate 332 comprises at least two materials, such as first injectate 332a, second injectate 332b and/or third injectate 332c. First injectate 332a, second injectate 332b and/or third injectate 332c can comprise similar or dissimilar properties. In some embodiments, first injectate 332a and second injectate 332b can be constructed and arranged to undergo at least one of a chemical change or a physical change when brought into contact with each other, such as in a polymerization reaction as described herebelow. System 10 can be constructed and arranged such that a chemical and/or physical change occurs after first injectate 332a and second injectate 332b make contact with each other within one or more tissue layers, such as one or more layers of target tissue. The induced chemical and/or physical change can comprise a change selected from the group consisting of: forming a hydrogel; creating a material with a higher viscosity than either first injectate 332a or second injectate 332b; polymerizing first injectate 332a and/or second injectate 332b; and combinations of these. First injectate 332a, second injectate 332b and/or third injectate 332c can be delivered simultaneously or sequentially, via the same or different delivery elements 140.

In some embodiments, second injectate 332b is constructed and arranged to remain within or proximate the therapeutic restriction TR for a longer time period than first injectate 332a (e.g. second injectate 332b is absorbed, degrades, migrates and/or otherwise is reduced from within the therapeutic restriction TR or tissue proximate the therapeutic restriction TR at a slower rate than first injectate 332a). In these embodiments, first injectate 332a and second injectate 332b can be delivered to target tissue in the same procedure or different procedures, such as when second injectate 332b is delivered at least one day after the delivery of first injectate 332a, to similar target tissue or different target tissue (e.g. to similar or dissimilar locations of target tissue).

In some embodiments, injectate 332 comprises ethylene vinyl alcohol (EVOH). In these embodiments, injectate 332 can further comprise one or more other materials, such as a material selected from the group consisting of: dimethyl sulfoxide (DMSO); a material constructed and arranged to polymerize EVOH; saline; and combinations of these. In some embodiments, first injectate 332a comprises EVOH which is delivered by a first delivery element 140 (e.g. a first needle), and second injectate 332b comprising saline or another EVOH polymerizing material is delivered by a second delivery element 140 (e.g. a second needle). In other embodiments, a single delivery element 140 comprises a needle with two lumens, a first lumen for delivering first injectate 332a and a second lumen for delivering second injectate 332b. In these embodiments, IDU 330 and/or functional element 139 can comprise one or more heating elements configured to heat at least the EVOH material. System 10 can be constructed and arranged to heat an injectate 332 such as EVOH to a temperature of at least 50° C. or at least 60° C. In some embodiments, injectate 332 is heated to a temperature below a threshold that would cause damage to tissue of a muscularis layer of the GI tract. Injectate 332 can be heated prior to its delivery into target tissue by one or more delivery elements 140. In some embodiments, functional element 139 comprises a heating element positioned on, in or within shaft 101 and configured to heat injectate 332 such as an injectate comprising at least EVOH. Alternatively or additionally, a functional element 139 comprising a heating element can be positioned in handle 110 and configured to heat injectate 332. Alternatively or additionally, one or more heaters 333 of IDU 330 can heat one or more injectates 332 prior to delivery of the one or more injectates 332 to device 100.

Injectate 332 can comprise a material selected from the group consisting of: a peptide polymer; polylactic acid; polymethylmethacrylate (PMMA); a hydrogel; and combinations of these. Injectate 332 can comprise a material configured to expand after delivery into target tissue, such as a hydrogel configured to expand after delivery.

In some embodiments, injectate 332 comprises a material harvested from a mammalian body, as described hereabove in reference to the method of FIG. 1. In these embodiments, injectate 332 can comprise autologous material harvested from the patient. Injectate 332 can comprise harvested material selected from the group consisting of: fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; and combinations of these. Injectate 332 can comprise a peptide polymer configured to stimulate fibroblasts to produce collagen.

Injectate 332 can comprise a sclerosant and/or an adhesive such as cyanoacrylate. Injectate 332 can comprise one or more agents configured to elute into tissue over time, such as a pharmaceutical agent that is released from injectate 332 over time. Injectate 332 can comprise one or more materials used to visualize injectate 332 and/or a therapeutic restriction TR, such as a radiopaque material, an ultrasonically reflective material, and/or a visible material such as a visible dye.

In some embodiments, system 10 comprises a sizing device 430 used to measure the lumen of one or more segments of the GI tract and/or to measure a dimensional parameter of a therapeutic restriction TR (e.g. the inner diameter of therapeutic restriction TR which represents the outer diameter of the opening present within therapeutic restriction TR), such as to produce luminal data. Sizing device 430 can comprise a sizing device of similar construction and arrangement to the sizing device described in applicant's co-pending International Patent Application Serial Number PCT/US2014/055514, entitled "Systems, Methods and Devices for Treatment of Target Tissue", filed Sep. 12, 2014, the contents of which is incorporated herein by reference in its entirety. Sizing device 430 can be constructed and arranged to measure luminal diameter information prior to the creation of a therapeutic restriction TR (e.g. prior to delivery of injectate 332 into tissue). Alternatively or additionally, sizing device 430 can be constructed and arranged to measure luminal diameter and/or therapeutic restriction TR size information during and/or after creation of a therapeutic restriction TR, such as to monitor or determine a therapeutic restriction TR parameter. Luminal data collected with sizing device 430 can be used to perform a function selected from the group consisting of: sizing of expandable assembly 130; determining a volume of injectate 332 to be delivered; determining a composition (e.g. selection and or ratio of multiple materials) of injectate 332 to be delivered; determining a therapeutic restriction TR parameter such as inner diameter, pressure and/or volume; determining the pressure required to advance (e.g. push) sizing device 430 through the GI tract beyond the therapeutic restriction TR; and combinations of these.

In some embodiments, IDU 330 or another component of system 10 comprises one or more algorithms configured to determine a therapeutic restriction TR parameter, such as the amount (e.g. volume and/or mass) of injectate 332 to be delivered or a dimensional parameter of therapeutic restriction TR (e.g. length, width, thickness, volume, etc). In some embodiments, system 10 is constructed and arranged to create multiple therapeutic restrictions TR, such as multiple therapeutic restrictions created in a single clinical procedure or multiple clinical procedures, as described hereabove in reference to FIG. 1. In some embodiments, system 10 is constructed and arranged to adjust the volume of a therapeutic restriction TR, such as an adjustment that occurs in the same clinical procedure as the creation of the therapeutic restriction TR or in a subsequent clinical procedure.

Referring now to FIGS. 3A-3D, side and end sectional views of four therapeutic restrictions are illustrated, consistent with the present inventive concepts. FIG. 3A-3D illustrate therapeutic restrictions TR1, TR2, TR3a, TR3b, TR3c and TR4 (singly or collectively therapeutic restriction TR). The therapeutic restriction TR of the present inventive concepts can comprise various sizes and geometries, and can comprise a combination of injectate and repositioned tissue. In some embodiments, one or more therapeutic restrictions TR comprise a cumulative axial length (e.g. axial length of a single therapeutic restriction TR or sum of axial length of multiple therapeutic restrictions TR) between 1 mm and 100 mm, such as a cumulative axial length between 1 mm and 20 mm. A therapeutic restriction TR can comprise an inner diameter (i.e. outer diameter of the opening) less than or equal to 10 mm, such as an inner diameter less than or equal to 5 mm, 4 mm, 3 mm, 2 mm or 1 mm. A therapeutic restriction TR can comprise an inner diameter that is between 1% and 50% of the inner diameter of the associated GI luminal segment prior to the delivering of the injectate, and the inner diameter can increase over time (e.g. as the injectate is absorbed, degrades, migrates and/or otherwise is reduced from within the therapeutic restriction TR or tissue proximate the therapeutic restriction TR). The system and/or injectate can be constructed and arranged such that the inner diameter of a therapeutic restriction TR increases to a diameter between 11% and 50% of the pre-treated GI luminal segment inner diameter, such as an increase in diameter that occurs during a time period of less than 1 year or less than 6 months. In some embodiments, at the time of creation of a therapeutic restriction TR, its inner diameter is between 1% and 20%, between 1% and 10%, or between 1% and 5% of the pre-treated GI luminal segment inner diameter.

In some embodiments, a therapeutic restriction TR comprises a substantially full circumferential geometry, such as therapeutic restriction TR1 of FIG. 3A. In some embodiments, a therapeutic restriction TR comprises a partial circumferential geometry, such as therapeutic restriction TR2 of FIG. 3B. In some embodiments, a therapeutic restriction TR comprises a relatively linear geometry, such as one of therapeutic restrictions TR3a, TR3b and TR3c shown in FIG. 3C and positioned such that their major axis is parallel with the axis of the GI segment. In some embodiments, a therapeutic restriction TR comprises a helical geometry, such as therapeutic restriction TR4 shown in FIG. 3D.

Referring now to FIGS. 4-10, a series of anatomical views showing various locations for the creation of a therapeutic restriction are illustrated, consistent with the present inventive concepts. The therapeutic restrictions TR of FIGS. 4-10 can be created using the method described hereabove in reference to FIG. 1, and the injectate delivery device 100 and/or system 10 described hereabove in reference to FIG. 2. The therapeutic restrictions TR of FIGS. 4-10 can each comprise multiple therapeutic restrictions TR.

Figure 4:
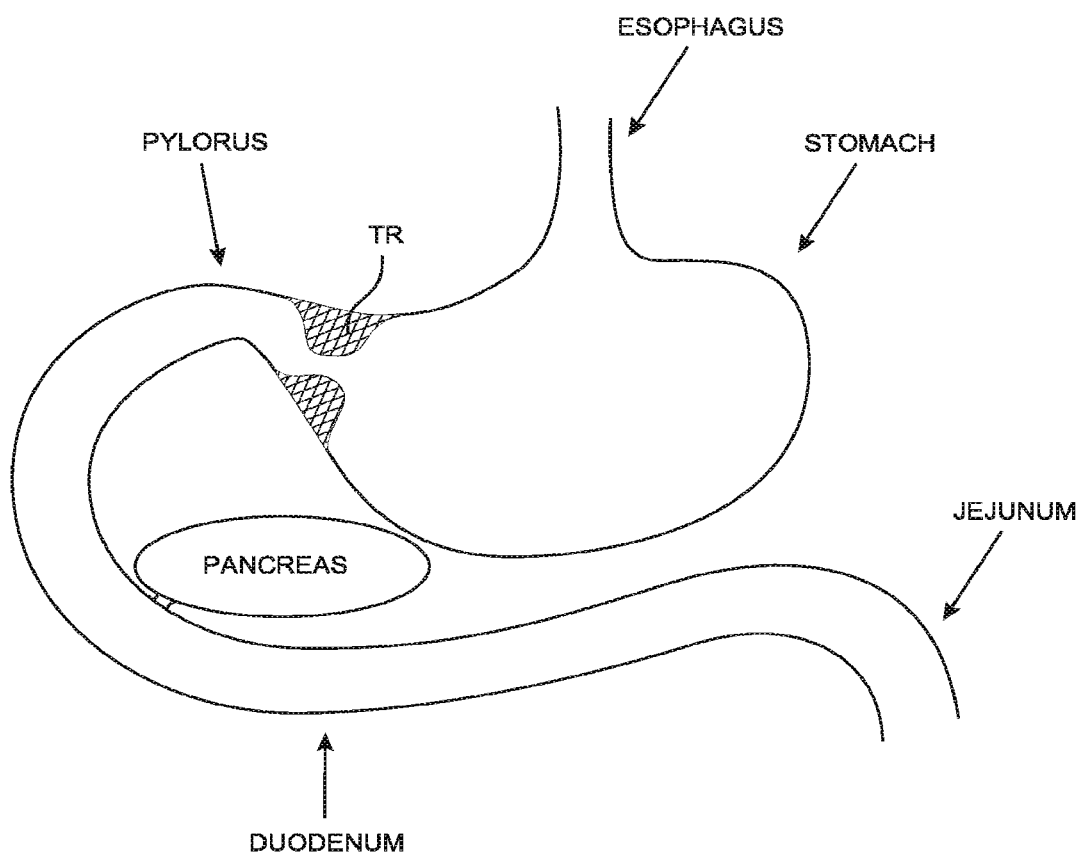
FIGS. 4-6 are a series of anatomical views showing various locations for the creation of a therapeutic restriction, consistent with the present inventive concepts.

In FIG. 4, a therapeutic restriction TR has been created at a location near but proximal to the pylorus. In the embodiments of FIG. 4, the therapeutic restriction TR can be configured to perform a function selected from the group consisting of: narrow exit from the stomach; increase satiety; decrease caloric intake; cause weight loss; and combinations of these.

Figure 5:
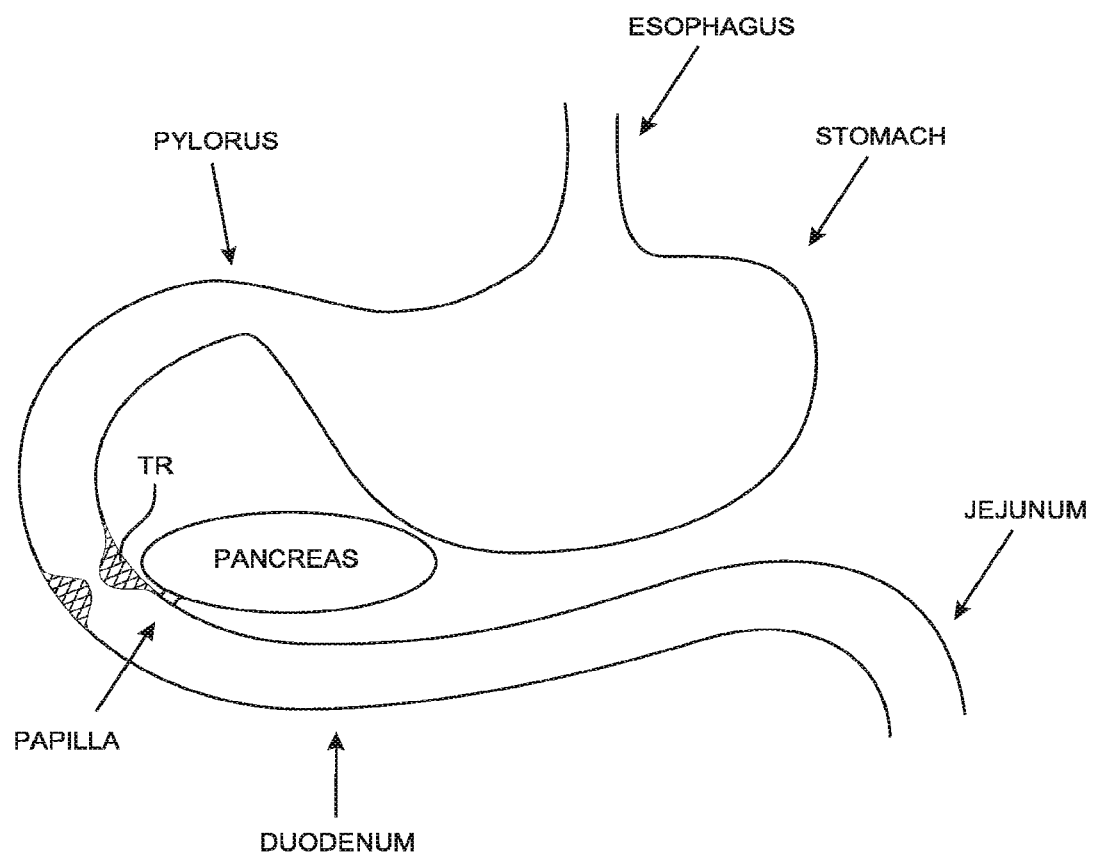

In FIG. 5, a therapeutic restriction TR has been created at a location near but proximal to the papilla (e.g. the major duodenal papilla and/or the minor duodenal papilla) In the embodiments of FIG. 5, the therapeutic restriction TR can be configured to perform a function selected from the group consisting of: narrow the lumen of a segment of duodenum, such as without altering an external duodenal dimension by taking advantage of small intestinal mucosal redundancy; create a clinical scenario resembling a gastric outlet obstruction; increase satiety; decrease caloric intake; cause weight loss; and combinations of these.

Figure 6:
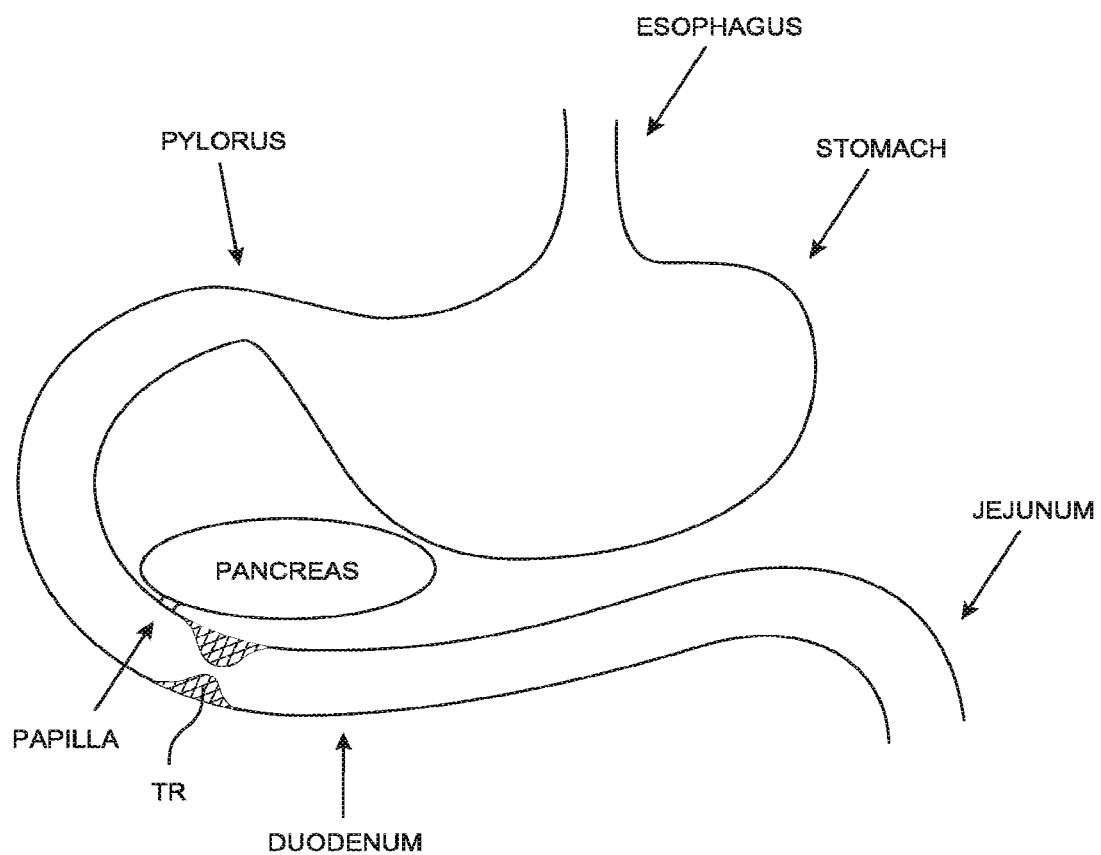

In FIG. 6, a therapeutic restriction TR has been created at a location near but distal to the papilla (e.g. the major duodenal papilla and/or the minor duodenal papilla). In the embodiments of FIG. 6, the therapeutic restriction TR can be configured to perform a function selected from the group consisting of: narrow the lumen of a duodenal segment, such as without altering an external duodenal dimension by taking advantage of small intestinal mucosal redundancy; create a clinical scenario resembling a gastric outlet obstruction; increase satiety; decrease caloric intake; cause weight loss; and combinations of these.

Figure 7:
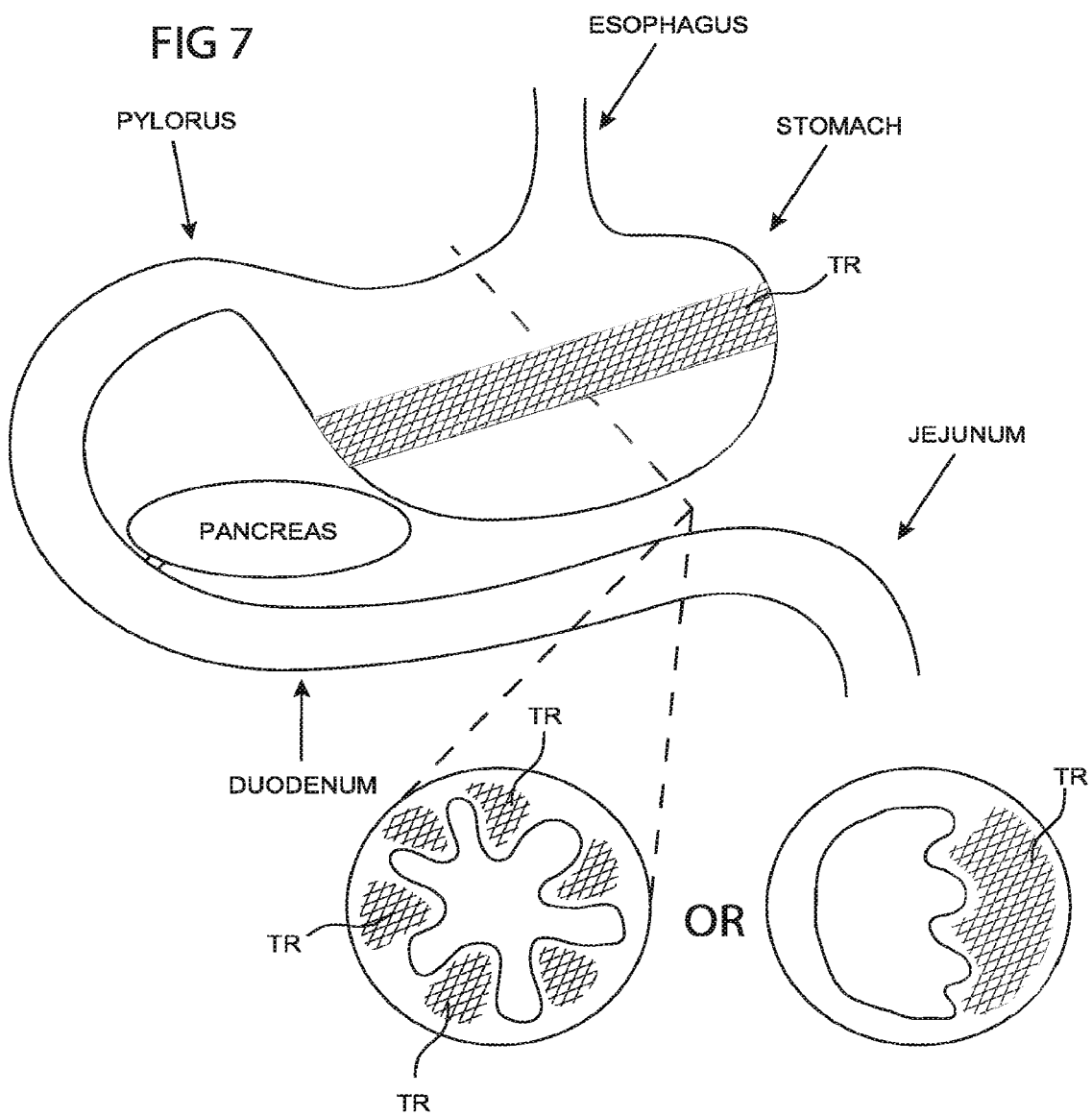
FIG. 7 is a view of a stomach.

In FIG. 7, a therapeutic restriction TR has been created along a portion of the stomach. In some embodiments, multiple therapeutic restrictions TR can be created about a full or at least near full circumference of the stomach, as shown in the cross section of the stomach illustrated in FIG. 7A. Alternatively, one or more therapeutic restrictions TR can be created about a circumferential portion (e.g. an approximate 180° portion) of the stomach, as shown in the cross section of the stomach illustrated in FIG. 7B. In the embodiments of FIGS. 7, 7A and 7B, one or more therapeutic restrictions TR can comprise arrays of therapeutic restrictions TR, such as linear arrays of multiple elongate therapeutic restrictions TR. In the embodiments of FIGS. 7, 7A and 7B, one or more therapeutic restrictions TR can be configured to perform a function selected from the group consisting of: reduce the volume of the stomach; alter gastric hormonal signaling such as to increase satiety and/or decrease caloric intake; and combinations of these.

Figure 8:
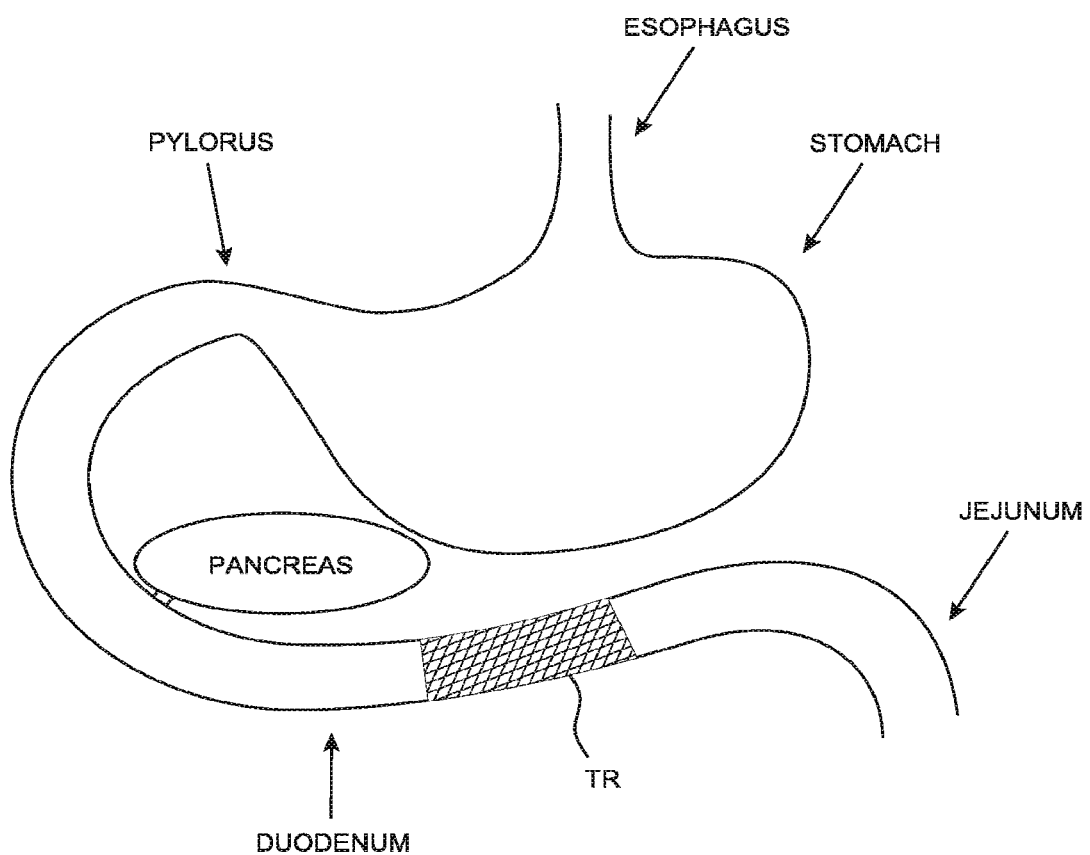
FIGS. 8-10 are a series of anatomical views showing various locations for the creation of a therapeutic restriction, consistent with the present inventive concepts.

In FIG. 8, a therapeutic restriction TR has been created in the duodenum. In the embodiments of FIG. 8, the therapeutic restriction TR can comprise one or more circumferential, partial circumferential, helical and/or linear expansions of tissue. In the embodiments of FIG. 8, the therapeutic restriction TR can be configured to perform a function selected from the group consisting of: narrow the lumen of a duodenal segment; reduce the mucosal surface area over a length of intestine; alter mucosal absorption; alter hormonal secretions; increase satiety; decrease caloric intake; cause weight loss; and combinations of these.

Figure 9:
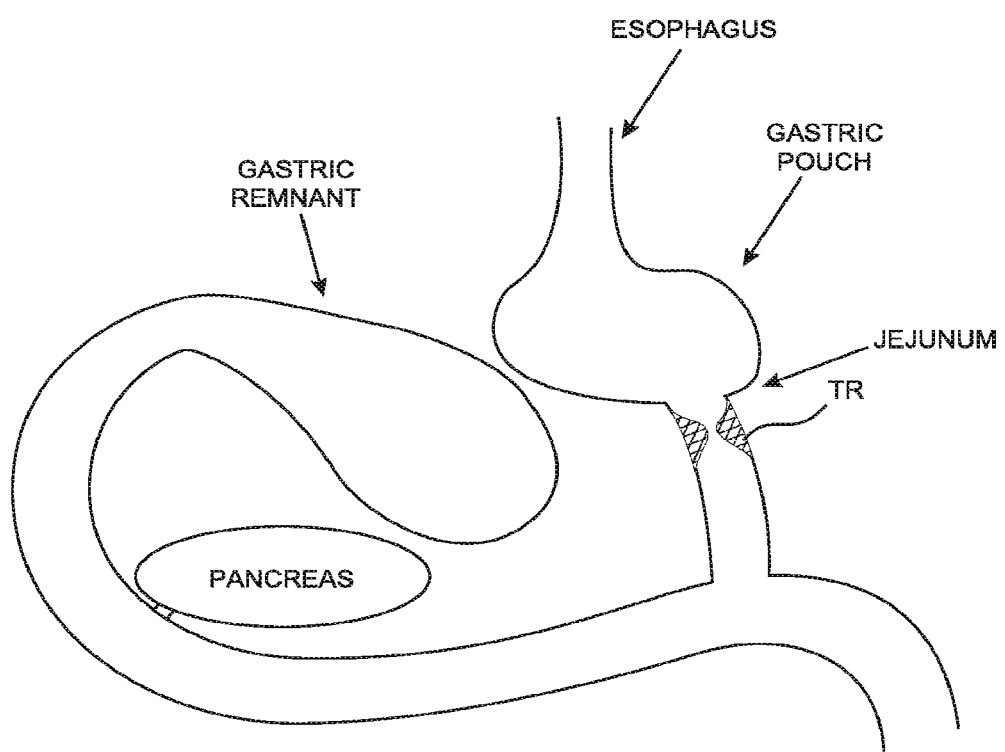

In FIG. 9, a therapeutic restriction TR has been created in a proximal portion of the jejunum, in a patient that has received a Roux-en-Y gastric bypass (RYGB) procedure. Patients that undergo RYGB procedures often regain weight, such as an increase in weight due to expansion of the gastric pouch and/or expansion of the gastrojejunal anastomosis. Alternatively or additionally, a therapeutic restriction TR can be created within the gastric pouch. In the embodiments of FIG. 9, the therapeutic restriction TR can be configured to perform a function selected from the group consisting of: improve the therapeutic benefit of an RYGB procedure; create a gastric pouch outlet obstruction; increase satiety; decrease caloric intake; cause weight loss; and combinations of these.

Figure 10:
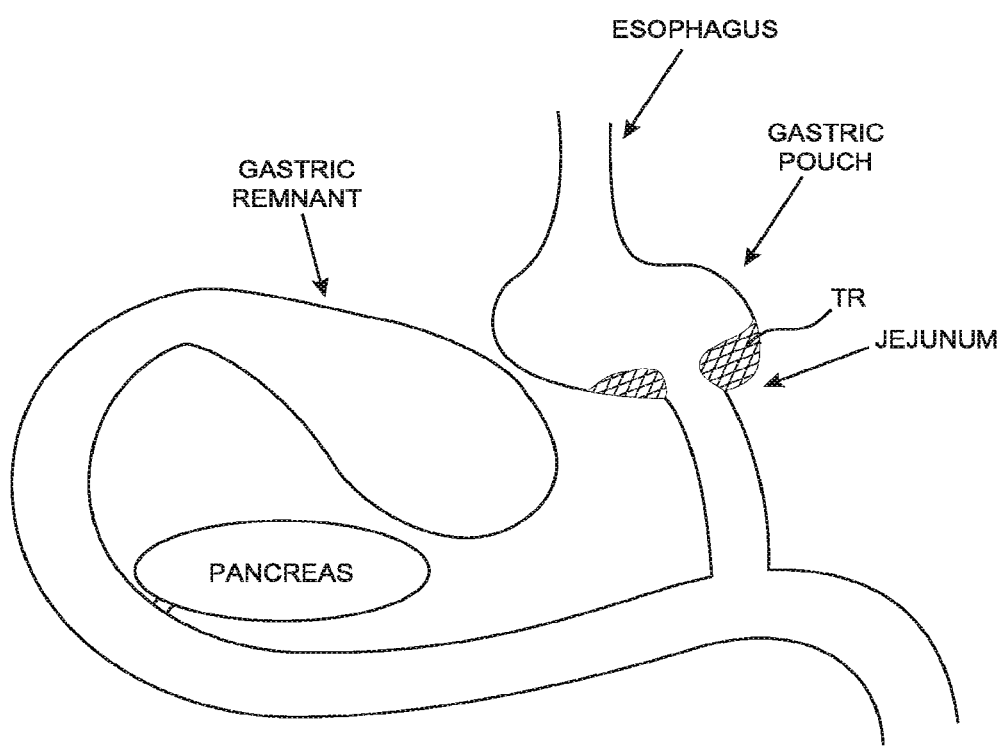

In FIG. 10, a therapeutic restriction TR has been created proximal to a gastrojejunal anastomosis and/or within a gastrojejunal anastomosis, in a patient that has received a Roux-en-Y gastric bypass (RYGB) procedure. Patients that undergo RYGB procedures often regain weight, such as an increase in weight due to expansion of the gastric pouch and/or expansion of the gastrojejunal anastomosis. In the embodiments of FIG. 10, the therapeutic restriction TR can be configured to perform a function selected from the group consisting of: improve the therapeutic benefit of an RYGB procedure; create a gastric pouch outlet obstruction; increase satiety; decrease caloric intake; cause weight loss; and combinations of these.

Referring now to FIGS. 11A-11D, a series of side and end sectional views of a segment of the gastrointestinal tract is illustrated: prior to creation of a therapeutic restriction; after creation of a therapeutic restriction; after a time period in which the therapeutic restriction has partially decreased; and after a time period in which the therapeutic restriction has fully reduced; respectively, consistent with the present inventive concepts. Injectate delivered to create a therapeutic restriction TR can be constructed and arranged such that the volume of the therapeutic restriction TR decreases over time, such as when the injectate is absorbed, degrades, migrates and/or otherwise is reduced from within the therapeutic restriction TR over time. Rates of therapeutic restriction TR volume decrease are described in detail hereabove in reference to FIGS. 2 and 3A-3D.

In FIG. 11A, side and end sectional views of a pre-treated segment of the GI tract is illustrated, such as a segment of the duodenum or jejunum with a luminal diameter $D_{pre}$ as shown. In FIG. 11B, a therapeutic restriction TR comprising a full or near full circumferential restriction has been created as shown, resulting in a reduced luminal diameter $D_{r1}$. In FIG. 11C, time has elapsed since the creation of TR shown in FIG. 11B, and the therapeutic restriction volume has reduced such that reduced volume therapeutic restriction TR' results in a diameter increase (restriction reduction) to diameter $D_{r2}$. In FIG. 11D, additional time has elapsed, such that no therapeutic restriction is present within the GI segment, and the luminal diameter $D_{post}$ approximates luminal diameter $D_{pre}$.

While the embodiments of FIGS. 11A-11D illustrate a luminal segment of the GI tract such as the duodenum or jejunum, other anatomical locations such as the stomach or an anastomotic site can include a therapeutic restriction TR that decreases in volume over time.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A system for treating a patient comprising:
a delivery device comprising:
an elongate shaft with a distal portion and at least one delivery element positioned on the elongate shaft distal portion; and
an injectate configured to expand when delivered into tissue;
a sizing device configured to measure a luminal diameter; and
an injectate delivery unit configured to determine an amount of the injectate to be delivered based on the measured luminal diameter in order to narrow a lumen of a segment of an intestine to an inner diameter that is less than or equal to 10 mm;
wherein the delivery device is configured to deliver, based on the determined amount of injectate, the injectate through the at least one delivery element into luminal wall tissue of the intestine to narrow the lumen of the segment of the intestine to the inner diameter that is less than or equal to 10 mm.

2. The system according to claim 1, wherein the at least one delivery element comprises at least two delivery elements.

3. The system according to claim 2, wherein the at least two delivery elements comprises at least three delivery elements.

4. The system according to claim 1, wherein the injectate comprises at least two materials.

5. The system according to claim 1, wherein the delivery device is configured to deliver the injectate to narrow a lumen of a segment of the intestine to an inner diameter that is less than or equal to 5 mm.

6. The system according to claim 5, wherein the delivery device is configured to deliver the injectate to narrow a lumen of a segment of the intestine to an inner diameter that is less than or equal to 4 mm.

7. The system according to claim 6, wherein the delivery device is configured to deliver the injectate to narrow a lumen of a segment of the intestine to an inner diameter that is less than or equal to 3 mm.

8. The system according to claim 1, wherein the injectate comprises a material selected from the group consisting of: peptide polymer; polylactic acid; polymethylmethacrylate; hydrogel; sclerosant; adhesive; cyanoacrylate; and combinations thereof.

9. The system according to claim 1, wherein the injectate comprises a material selected from the group consisting of: fat cells; collagen; autologous collagen; bovine collagen; porcine collagen; bioengineered human collagen; dermis; a dermal filler; hyaluronic acid; conjugated hyaluronic acid; calcium hydroxylapatite; fibroblasts; and combinations thereof.

10. The system according to claim 1, wherein the injectate is further configured to polymerize when delivered into tissue.

11. The system according to claim 1, wherein the injectate comprises hyaluronic acid.

12. The system according to claim 2, wherein the luminal wall tissue comprises submucosal tissue.

* * * * *